United States Patent
Takahashi

(10) Patent No.: US 10,820,815 B2
(45) Date of Patent: Nov. 3, 2020

(54) BIOLOGICAL INFORMATION DETECTING DEVICE AND CONTROL METHOD FOR BIOLOGICAL INFORMATION DETECTING DEVICE

(71) Applicant: Seiko Epson Corporation, Tokyo (JP)

(72) Inventor: Yusuke Takahashi, Matsumoto (JP)

(73) Assignee: Seiko Epson Corporation (JP)

( * ) Notice: Subject to any disclaimer, the term of this patent is extended or adjusted under 35 U.S.C. 154(b) by 748 days.

(21) Appl. No.: 15/347,749

(22) Filed: Nov. 9, 2016

(65) Prior Publication Data
US 2017/0164851 A1    Jun. 15, 2017

(30) Foreign Application Priority Data

Dec. 11, 2015  (JP) ................................. 2015-242018

(51) Int. Cl.
*A61B 5/024* (2006.01)
*A61B 5/11* (2006.01)
*A61B 5/00* (2006.01)

(52) U.S. Cl.
CPC ...... *A61B 5/02438* (2013.01); *A61B 5/02427* (2013.01); *A61B 5/1123* (2013.01); *A61B 5/681* (2013.01); *A61B 5/721* (2013.01); *A61B 5/7207* (2013.01); *A61B 5/7214* (2013.01); *A61B 2560/0209* (2013.01); *A61B 2562/0219* (2013.01)

(58) Field of Classification Search
None
See application file for complete search history.

(56) References Cited

U.S. PATENT DOCUMENTS

2016/0058367 A1 *  3/2016  Raghuram ............. A61B 5/486
                                                      600/479
2018/0028080 A1 *  2/2018  Ouwerkerk .......... A61B 5/7207

FOREIGN PATENT DOCUMENTS

| JP | 2014-212915 A | 11/2014 |
| JP | 2015-188496 A | 11/2015 |
| WO | WO-2015-146139 A | 10/2015 |

* cited by examiner

*Primary Examiner* — John C Kuan
(74) *Attorney, Agent, or Firm* — Harness, Dickey & Pierce, P.L.C.

(57) ABSTRACT

A biological information detecting device includes at least one light emitting section, a first light receiving section, a second light receiving section, and a processing section configured to acquire biological information on the basis of at least one a first detection signal acquired from the first light receiving section and a second detection signal acquired from the second light receiving section. The processing section switches an operation mode to one of a first operation mode for acquiring the biological information on the basis of the first detection signal and the second detection signal and a second operation mode for acquiring the biological information on the basis of one detection signal of the first detection signal and the second detection signal.

20 Claims, 18 Drawing Sheets

BIOLOGICAL INFORMATION DETECTING DEVICE AND CONTROL METHOD FOR BIOLOGICAL INFORMATION DETECTING DEVICE

CROSS-REFERENCES TO RELATED APPLICATIONS

This application claims priority to Japanese Patent Application No. 2015-242018, filed Dec. 11, 2015, the entirety of which is herein incorporated by reference.

BACKGROUND

1. Technical Field

The present invention relates to a biological information detecting device, a control method for the biological information detecting device, and the like.

2. Related Art

There has been known a method of using, as a sensor for detecting biological information, a photoelectric sensor including a light emitting section that radiates light on a subject and a light receiving section that receives reflected light of the light radiated from the light emitting section and reflected on the subject. For example, there has been known a biological information detecting device, in a narrow sense, a pulse wave meter that acquires pulse wave information (information such as a pulse rate and a pulse interval) as biological information on the basis of biological information detected by a pulse wave sensor including a light emitting section and a light receiving section.

In particular, JP-A-2015-188496 (Patent Literature 1) discloses a biological information detecting device that uses a sensor unit (a pulse wave sensor section) including at least one light emitting section and a plurality of light receiving sections to acquire two detection signals and calculates biological information on the basis of the two detection signals.

JP-A-2015-188496 (Patent Literature 1) is an example of the related art.

JP-A-2014-212915 (Patent Literature 2) is an example of the related art.

As disclosed in Patent Literature 1, it is possible to improve detection accuracy of biological information by using two biological sensors (detecting sections or pulse wave sensors) including sets of light emitting sections and light receiving sections. This is because, for example, it is possible to appropriately reduce body motion noise that is not easily reduced by a body motion sensor such as an acceleration sensor.

However, since the two pulse wave sensors need to be operated, power consumption increases compared with when one pulse wave sensor is used. That is, always operating the two pulse wave sensors leads to a reduction in battery life. An investigation by the applicant has found that biological information can be detected at sufficient accuracy if one pulse wave sensor is used as in a situation in which body motion of a user is little.

That is, although it is desirable to operate one pulse wave sensor in some case or operate two pulse wave sensors in other cases depending on a situation, the methods in the past disclosed in Patent Literature 1 and the like do not take that point into account.

SUMMARY

An advantage of some aspects of the invention is to provide a biological information detecting device, a control method for the biological information detecting device, and the like that performs switching of an operation mode to realize an operation that takes into account a relation between detection accuracy of biological information and power consumption.

An aspect of the invention relates to a biological information detecting device including: at least one light emitting section configured to radiate light on a subject; a first light receiving section configured to receive light from the subject; a second light receiving section configured to receive the light from the subject; and a processing section configured to acquire biological information on the basis of at least one detection signal of a first detection signal acquired from the first light receiving section and a second detection signal acquired from the second light receiving section. The processing section switches an operation mode to one of a first operation mode for acquiring the biological information on the basis of the first detection signal and the second detection signal and a second operation mode for acquiring the biological information on the basis of one detection signal of the first detection signal and the second detection signal.

According to the aspect of the invention, in the biological information detecting device capable of acquiring the detection signals respectively from the two light receiving sections, switching processing is performed between the first operation mode for using both of the detection signals and the second operation mode for using one of the detection signals. Consequently, it is possible to, for example, set an operation mode corresponding to a situation taking into account both of detection accuracy of biological information and power consumption.

In the aspect of the invention, the processing section may perform the switching processing for the operation mode on the basis of a result of behavior determination processing for a user.

With this configuration, it is possible to perform the switching processing for the operation mode according to the result of the behavior determination processing.

In the aspect of the invention, the processing section may switch the operation mode from the first operation mode to the second operation mode when it is determined on the basis of the result of the behavior determination processing for the user that the user has changed to a running state or a walking state.

With this configuration, it is possible to use an appropriate operation mode corresponding to the running state or the walking state.

In the aspect of the invention, the processing section may set the operation mode to the first operation mode until a given time elapses after it is determined that the user has changed to the running state or the walking state on the basis of the result of the behavior determination processing for the user and switch the operation mode to the second operation mode after the given time elapses.

With this configuration, it is possible to use an appropriate operation mode even at, for example, a start time of the running state or the walking state.

In the aspect of the invention, the biological information detecting device may further include a body motion sensor section, and the processing section may perform the behavior determination processing on the basis of body motion information acquired from the body motion sensor section and perform the switching processing for the operation mode on the basis of the result of the behavior determination processing.

With this configuration, it is possible to perform the behavior determination processing in the biological information detecting device on the basis of the body motion information.

In the aspect of the invention, the processing section may perform the switching processing for the operation mode on the basis of a result of the behavior determination processing acquired from an external apparatus.

With this configuration, it is possible to acquire the result of the behavior determination processing from the external apparatus.

In the aspect of the invention, the processing section may switch the operation mode from the first operation mode to the second operation mode when a predetermined frequency component corresponding to repetitive exercise is detected.

With this configuration, it is possible to switch the operation mode on the basis of a result of frequency analysis processing.

In the aspect of the invention, the processing section may be capable of setting, as a measurement mode of the biological information detecting device, a plurality of measurement modes including at least two of an exercise measurement mode, a daily mode, and a sleep mode, and the processing section may perform the switching processing for the operation mode on the basis of the set measurement mode.

With this configuration, it is possible to switch the operation mode on the basis of the measurement mode of the biological information detecting device.

In the aspect of the invention, the processing section may perform the switching processing for the operation mode on the basis of operation information of the biological information detecting device.

With this configuration, it is possible to switch the operation mode on the basis of operation information.

In the aspect of the invention, the processing section may switch the operation mode to the first operation mode when it is determined on the basis of the operation information that the measurement mode is the exercise measurement mode.

With this configuration, it is possible to switch the operation mode on the basis of the operation information indicating that the measurement mode is the exercise measurement mode.

In the aspect of the invention, the biological information detecting device may further include a communication section configured to perform communication with an external apparatus, and the processing section may perform the switching processing for the operation mode on the basis of communication situation information of the communication section.

With this configuration, it is possible to switch the operation mode on the basis of the communication situation information.

In the aspect of the invention, the processing section may perform the switching processing for the operation mode on the basis of position information of the biological information detecting device.

With this configuration, it is possible to switch the operation mode on the basis of the position information.

In the aspect of the invention, the processing section may perform the switching processing for the operation mode on the basis of quality information of one detection signal of the first detection signal and the second detection signal.

With this configuration, it is possible to switch the operation mode on the basis of the quality information of the detection signal.

In the aspect of the invention, the processing section may perform the switching processing for the operation mode on the basis of a determination result of autocorrelation information of the one detection signal.

With this configuration, it is possible to use the autocorrelation information as the quality information.

In the aspect of the invention, the processing section may perform the switching processing for the operation mode on the basis of battery residual capacity information of a battery included in the biological information detecting device.

With this configuration, it is possible to switch the operation mode on the basis of a battery residual capacity.

In the aspect of the invention, the processing section may set the operation mode to the second operation mode in a measurement preparation period and perform the switching processing for the operation mode in a period after the measurement preparation period.

With this configuration, it is possible to fix the operation mode to the second operation mode in the measurement preparation period and thereafter start the switching processing for the operation mode.

Another aspect of the invention relates to a control method for a biological information detecting device including: at least one light emitting section configured to radiate light on a subject; a first light receiving section configured to receive light from the subject; and a second light receiving section configured to receive the light from the subject, the control method for the biological information detecting device comprising performing switching processing for switching an operation mode to one of a first operation mode for acquiring biological information on the basis of a first detection signal acquired from the first light receiving section and a second detection signal acquired from the second light receiving section and a second operation mode for acquiring the biological information on the basis of one detection signal of the first detection signal and the second detection signal.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
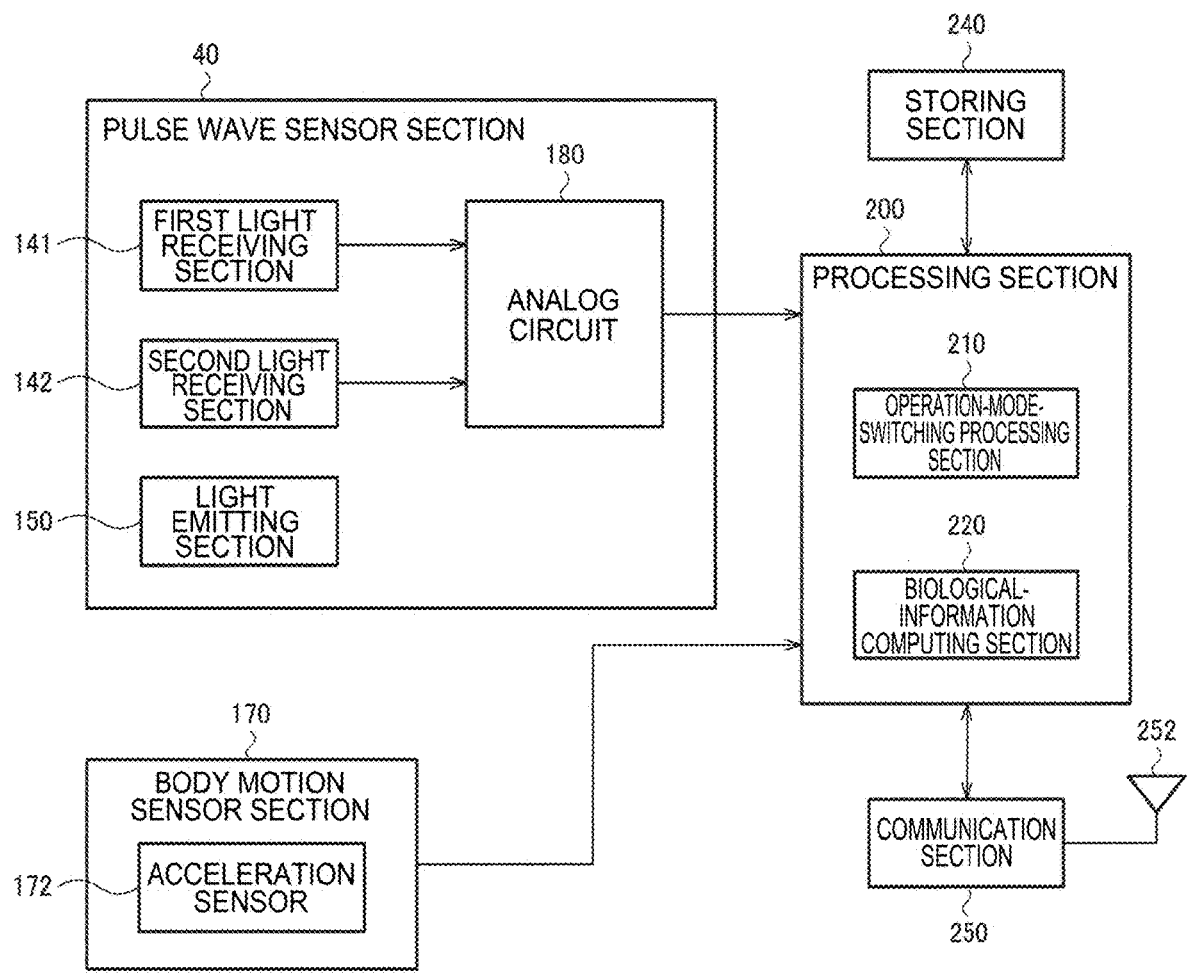
FIG. 1 is a configuration example of a biological information detecting device.

An embodiment is explained below. Note that the embodiment explained below does not unduly limit the contents of the invention described in the appended claims. Not all of components explained in the embodiment are essential constituent elements of the invention.

1. Method In The Embodiment

First, a method in the embodiment is explained. As disclosed in Patent Literature 1 and the like, there is known a biological information detecting device including a plurality of biological sensors (pulse wave sensors) including light emitting sections and light receiving sections.

Note that each of the light emitting sections and the light receiving sections may be provided by a number corresponding to the number of the pulse wave sensors. For example, a first pulse wave sensor is realized by a first light emitting section and a first light receiving section. A second pulse wave sensor is realized by a second light emitting section and a second light receiving section. Alternatively, the plurality of pulse wave sensors can share the light emitting section. For example, the first pulse wave sensor may be realized by the light emitting section and the first light receiving section. The second pulse wave sensor may be realized by the light emitting section, which is the same as the light emitting section of the first pulse wave sensor, and the second light receiving section. Besides, various modified implementations are possible concerning specific components for realizing the plurality of pulse wave sensors.

In the following explanation, in this specification, in particular, an example including two pulse wave sensors is considered. Therefore, an operation mode of a biological information detecting device capable of using both of detection signals (a first detection signal and a second detection signal) acquired from two pulse wave sensors is referred to as double sensor mode. As comparison with the double sensor mode, an operation mode of a biological information detecting device capable of using a detection signal acquired from one pulse wave sensor is referred to as single sensor mode.

As disclosed in Patent Literature 1 and the like, in the double sensor mode, it is possible to accurately detect biological information compared with the single sensor mode. Note that an example is explained below in which pulse wave information is detected as the biological information. Specifically, this is because, by differentiating a sensitivity characteristic to a pulse in the first detection signal acquired from the first light receiving section and the second detection signal acquired from the second light receiving section, it is possible to realize more appropriate noise reduction processing. Note that, in order to differentiate pulse sensitivity, pressing pressures on a subject corresponding to the pulse wave sensors only have to be differentiated or the distance between the light emitting section and light receiving section only has to be differentiated. Specific configuration examples are explained below with reference to FIGS. 12A to 19.

There is known body motion noise as noise included in a pulse wave sensor. For example, when a biological information detecting device is a device worn on a wrist of a subject as explained below with reference to FIG. 4 and the like, an arm swinging motion is a factor of the body motion noise. However, the arm swinging motion can be detected by a body motion sensor such as an acceleration sensor. Therefore, if the biological information detecting device is operated in the single sensor mode and noise reduction processing using body motion information acquired from the body motion sensor is performed, the body motion noise due to the arm swinging motion can be reduced to a certain degree (if the arm swing is not hard or has periodicity). The noise reduction processing is, for example, adaptive filter processing explained below with reference to FIG. 6.

However, in the case of a hand gripping and opening motion, since movement by the motion is small, the body motion information cannot be used as a reference of the body motion noise. As a result, even if the noise reduction processing using the body motion information is performed, it is difficult to reduce, in a sufficient level, the body motion noise due to the gripping motion.

In that regard, in the double sensor mode, both of the first detection signal and the second detection signal are detected using a photoelectric sensor. Since the first detection signal and the second detection signal are signals due to reflected light on an organism, a noise component included in one detection signal is also included in the other detection signal. Specifically, the body motion noise due to the gripping motion is included in both of the first detection signal and the second detection signal. Further, if noise other than the body motion noise could be included in the first detection signal detected by the photoelectric sensor, the noise is also included in the second detection signal detected by a photoelectric sensor having the same configuration.

In the first light receiving section, sensitivity of a pulse signal is set high to mainly acquire a detection signal including a pulse component. In the second light receiving section, sensitivity of a pulse signal is set low and sensitivity of body motion noise is set high intentionally to mainly acquire a detection signal including a body motion noise. If a signal corresponding to the body motion noise can be detected in the second light receiving section, it is possible to reduce the body motion noise by removing (reducing) a component corresponding to the detection signal in the second light receiving section from the detection signal in the first light receiving section. In this case, since the sensitivity of the pulse signal is low in the second light receiving section, even a pulse component included in the detection signal of the first light receiving section is not excessively reduced. Note that, specifically, the noise reduction processing only has to be using a spectrum subtraction method or the like. Details are explained below.

As explained above, in the double sensor mode, compared with the single sensor mode, it is possible to, for example, increase types of noise that can be removed. Therefore, in terms of noise reducing performance, the double sensor mode is superior to the single sensor mode.

However, in the double sensor mode, power consumption increases compared with the single sensor mode. For example, it is necessary to operate two systems of amplifiers, which amplify sensor signals, and A/D converters. Further, processing for digital data also increases. This leads to an increase in power consumption and a processing load in a processing section realized by a DSP or the like. Depending on the number of light emitting sections and setting of control of operation timing (e.g., concerning whether the first detection signal and the second detection signal are simultaneously acquired or alternately acquired), it is conceivable that power consumption in the light emitting sections increases because a light emission frequency (duty) of the light emitting sections increases and light emission intensity of the light emitting sections increases.

It is also assumed that the biological information detecting device according to this embodiment detects biological information in a long period (in a narrow sense, in one day) including work time and sleep time rather than detecting biological information only under a specific situation (e.g., during exercise) and utilizes the biological information as a "life log". In such a case, it is important that the biological information detecting device can continuously operate as long a period as possible. Therefore, in some case, the increase in power consumption could be a problem.

In a method in the past including two pulse wave sensors in terms of hardware such as Patent Literature 1, it is assumed that the two pulse wave sensors are always operated from a viewpoint of putting importance on accuracy. There is no disclosure from the viewpoint of putting importance on power consumption. There is no disclosure concerning a method of intentionally not operating one of the two pulse wave sensors.

Therefore, this embodiment proposes a method of switching the double sensor mode and the single sensor mode according to a situation. Specifically, the biological information detecting device according to this embodiment includes, as shown in FIG. 1, at least one light emitting section (light emitting sensor device) 150 that radiates light on a subject, a first light receiving section (a light receiving sensor device) 141 that receives light from the subject, a second light receiving section 142 that receives the light from the subject, and a processing section (a processor) 200 that acquires biological information on the basis of at least one detection signal of a first detection signal acquired from the first light receiving section 141 and a second detection signal acquired from the second light receiving section 142. The processing section 200 performs switching processing for switching an operation mode to one of a first operation mode for acquiring the biological information on the basis of the first detection signal and the second detection signal and a second operation mode for acquiring the biological information on the basis of one detection signal of the first detection signal and the second detection signal.

Note that, as explained above, the light emitting section 150 is not limited to one light emitting section and may be two or more light emitting sections. The light receiving sections may be three or more light receiving sections. The first operation mode corresponds to the double sensor mode. The second operation mode corresponds to the single sensor mode. In the following explanation, the double sensor mode and the single sensor mode in this specification can be respectively considered as being expanded to the first operation mode and the second operation mode. In the following explanation, it is assumed that the biological information is calculated on the first detection signal in the second operation mode. However, the second detection signal may be used. That is, in the following explanation, the first detection signal is assumed to be a signal relatively having high pulse sensitivity and the second detection signal is assumed to be a signal relatively having low pulse sensitivity. However, the first detection signal and the second detection signal may be opposite.

Consequently, by providing the two light receiving sections as hardware components, it is possible to perform operation in the single sensor mode by not using one detection signal of the first and second detection signals while making it possible to perform operation in the double sensor mode. That is, by switching the double sensor mode and the single sensor mode according to a situation, it is possible to realize the operation of the biological information detecting device that takes into account both of detection accuracy of biological information and power consumption. Specifically, the operation mode is switched to the double sensor mode when highly accurate detection processing for biological information is necessary, for example, when it is assumed that there are a lot of noise components. On the other hand, for example, when there are few noise components, battery life can be increased by switching the operation mode to the single sensor mode and reducing power consumption.

Note that, in the single sensor mode, since the second detection signal is not used, it is possible to reduce at least power consumption and a processing load in the processing section 200. However, since the second detection signal is not used, an output itself of the second detection signal is unnecessary. It is possible to perform more efficient power saving by stopping the operation of a component for output. For example, in an example in which the second light emitting section is provided, the second light emitting section can be stopped. A route for an output of the second detection signal in an analog circuit (an amplifier, an A/D converter, etc.) can be stopped. In the following explanation, it is assumed that, in the single sensor mode, an analog circuit or the like for an output of the second detection signal is also stopped.

In the following explanation, a configuration example of the biological information detecting device according to this embodiment is explained. Thereafter, a specific switching method for the double sensor mode and the single sensor mode is explained. Finally, a specific configuration example of a pulse wave sensor section capable of acquiring the first and second detection signals is explained.

Figure 2A:
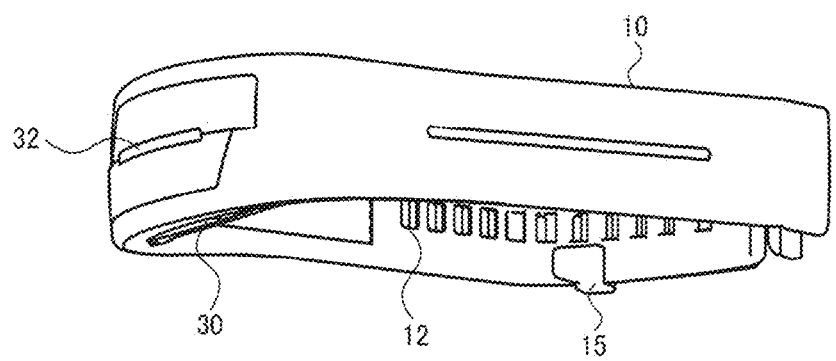
FIGS. 2A and 2B are exterior views of the biological information detecting device in an embodiment.
Figure 2B:
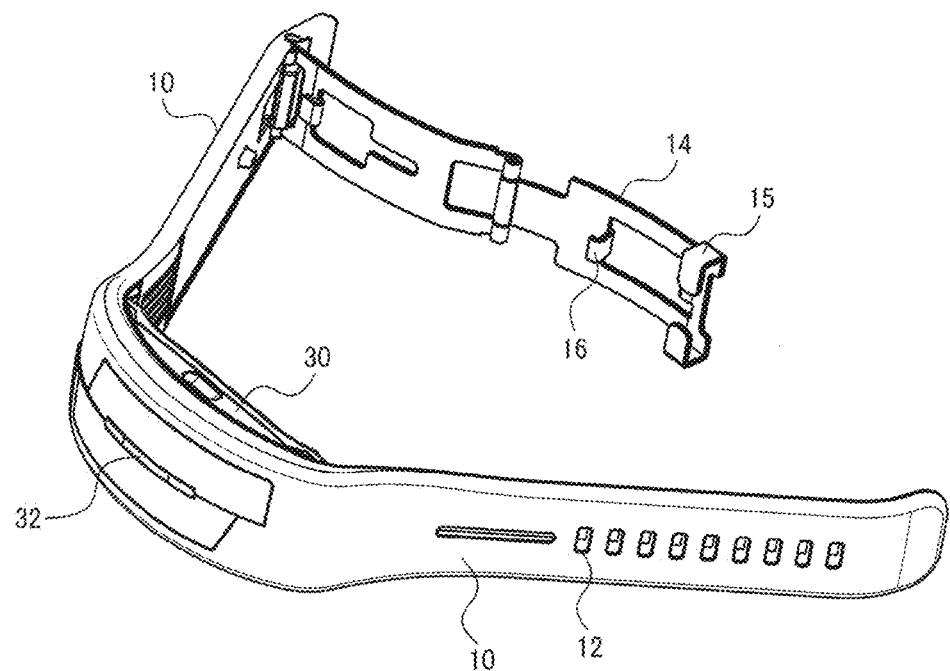
Figure 3:
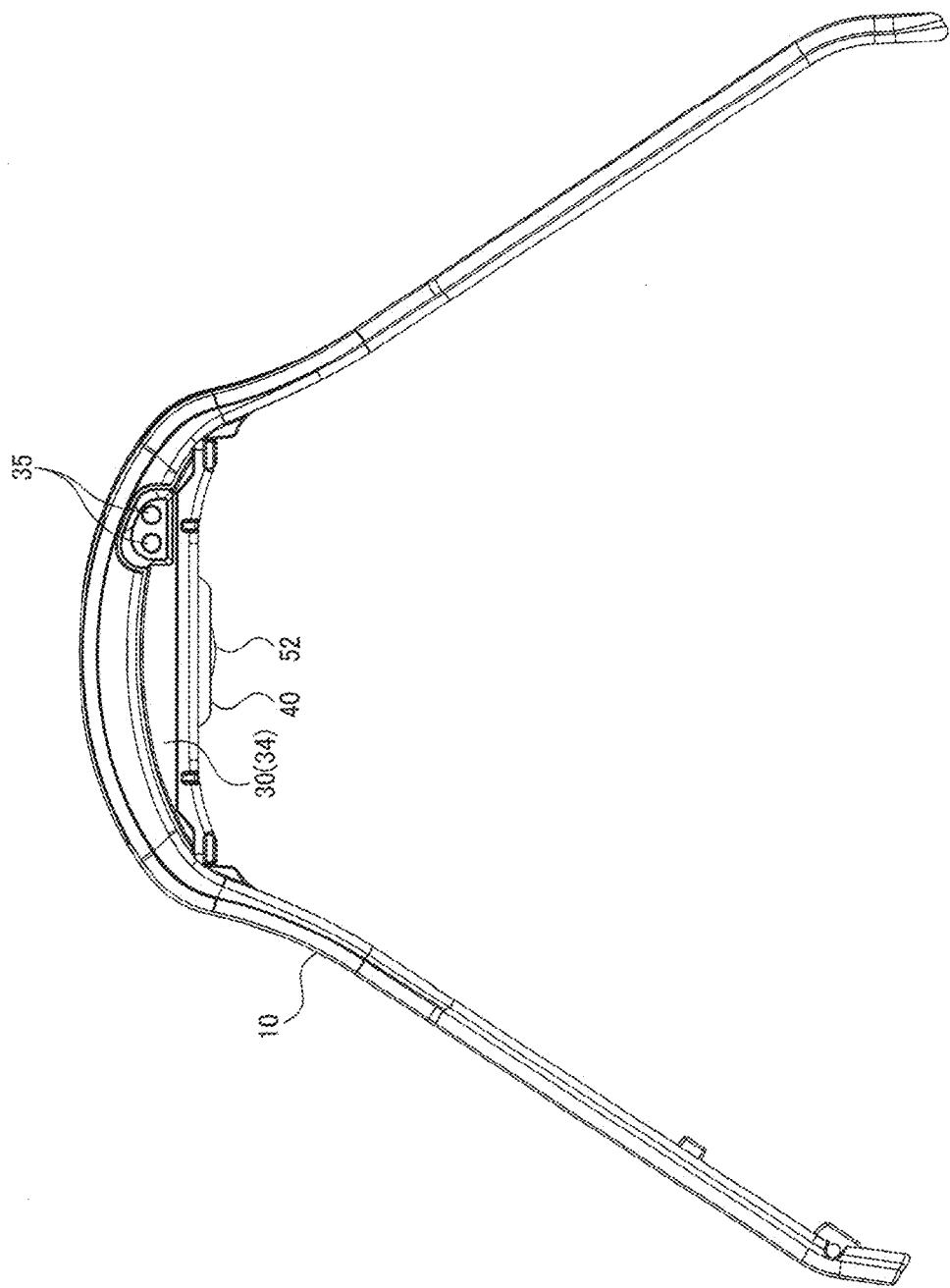
FIG. 3 is an exterior view of the biological information detecting device in the embodiment.

2. System Configuration Example 2.1 Overall Configuration Example of the Biological Information Detecting Device In FIGS. 2A, 2B, and 3, exterior views of a biological information detecting device 400 (a biological information measuring device) in this embodiment are shown. FIG. 2A is a view of the biological information detecting device 400 viewed from a front direction. FIG. 2B is a view of the biological information detecting device 400 viewed from an upward direction. FIG. 3 is a view of the biological information detecting device 400 viewed from a side direction.

As shown in FIG. 2A to 3, the biological information detecting device 400 in this embodiment includes a band section 10, a case section 30, and a pulse wave sensor section (a pulse wave sensor device) 40. The case section 30 is attached to the band section 10. The pulse wave sensor section 40 is provided in the case section 30. As shown in FIG. 1, the biological information detecting device 400 includes the processing section 200. The processing section 200 is provided in the case section 30 and detects biological information on the basis of a detection signal acquired from the pulse wave sensor section 40. Note that the biological information detecting device 400 in this embodiment is not limited to the configuration shown in FIGS. 2A to 3. Various modified implementations such as omission of a part of the components, replacement with other components, and addition of other components are possible.

The band section 10 is worn on a wrist of a user to wear the biological information detecting device 400. The band section 10 includes band holes 12 and a buckle section 14. The buckle section 14 includes a band inserting section 15 and a protrusion section 16. The user inserts one end side of the band section 10 into the band inserting section 15 of the buckle section 14 and inserts the protrusion section 16 of the buckle section 14 into the band hole 12 of the band section 10 to wear the biological information detecting device 400 on the wrist. In this case, the magnitude of a pressing pressure (a pressing pressure on the wrist surface) of the pulse wave sensor section 40 explained below is adjusted according to into which of the band holes 12 the protrusion section 16 is inserted. Note that the band section 10 may be configured to include a buckle instead of the buckle section 14.

The case section 30 is equivalent to a main body section of the biological information detecting device 400. On the inside of the case section 30, various components of the biological information detecting device 400 such as the pulse wave sensor section 40 and the processing section 200 are provided. That is, the case section 30 is a housing that houses these components. The case section 30 includes, for example, a top case 34 and a bottom case. Note that the case 30 does not have to be a form separated into the top case 34 and the bottom case.

A light emission window section 32 is provided in the case section 30. The light emission window section 32 is formed by a light transmitting member. In the case section 30, a light emitting section (an LED; a light emitting section for alarming different from the light emitting section 150 of a light detection unit) mounted on a flexible board. Light from the light emitting section is emitted to the outside of the case section 30 via the light emission window section 32.

As shown in FIG. 3, terminal sections 35 are provided in the case section 30. When the biological information detecting device 400 is attached to a not-shown cradle, terminal sections of the cradle and the terminal sections 35 of the case section 30 are electrically connected. Consequently, it is possible to charge a secondary battery (a battery) provided in the case section 30. Note that it is also possible to provide a terminal such as a micro USB in the biological information detecting device 400 and charge the secondary battery using a micro USB cable.

The pulse wave sensor section 40 detects biological information such as a pulse wave of the subject. For example, the pulse wave sensor section 40 includes, as shown in FIG. 1, the first light receiving section 141, the second light receiving section 142, the light emitting section 150, and an analog circuit 180. The analog circuit 180 can include an amplifier that performs amplification of outputs from the first light receiving section 141 and the second light receiving section 142 and an A/D converter that performs A/D conversion of the outputs. As the amplifier and the A/D converter, two systems for an output of the first detection signal and an output of the second detection signal may be provided. An analog circuit of one system may be used in time division.

As explained below with reference to FIG. 12A and the like, the pulse wave sensor section 40 includes a convex section 52 that is formed by a light transmitting member 50 and comes into contact with the skin surface of the subject and applies a pressing pressure to the skin surface. In a state in which the convex section 52 applies the pressing pressure to the skin surface, the light emitting section 150 emits light and the light receiving sections receive the light reflected on the subject (a blood vessel). In the double sensor mode, the first light receiving section 141 and the second light receiving section 142 respectively receive reflected lights. Results of the light reception are output to the processing section 200 as the first detection signal and the second detection signal. In the single sensor mode, for example, light emission for light reception in the second light receiving section 142 is not performed. Alternatively, the second detection signal is not output because, for example, the amplifier and the A/D converter do not operate. Only the first detection signal is output to the processing section 200.

The processing section 200 performs two kinds of processing, that is, detection processing for biological information and switching processing for the operation mode. The detection processing for biological information is processing for calculating biological information on the basis of one or both of the first and second detection signals. Specifically, the processing section 200 performs noise reduction processing for the first detection signal and calculates pulse wave information such as a pulse rate and a pulse interval on the basis of the first detection signal after the noise reduction processing. Note that the biological information to be detected by the biological information detecting device in this embodiment is not limited to a pulse wave (a pulse rate). The biological information detecting device may be a device that detects biological information other than the pulse wave (e.g., oxygen saturation in blood, body temperature, or a heart rate). The switching processing for the operation mode is processing for switching the double sensor mode and the single sensor mode. Details of the switching processing are explained below.

Figure 4:
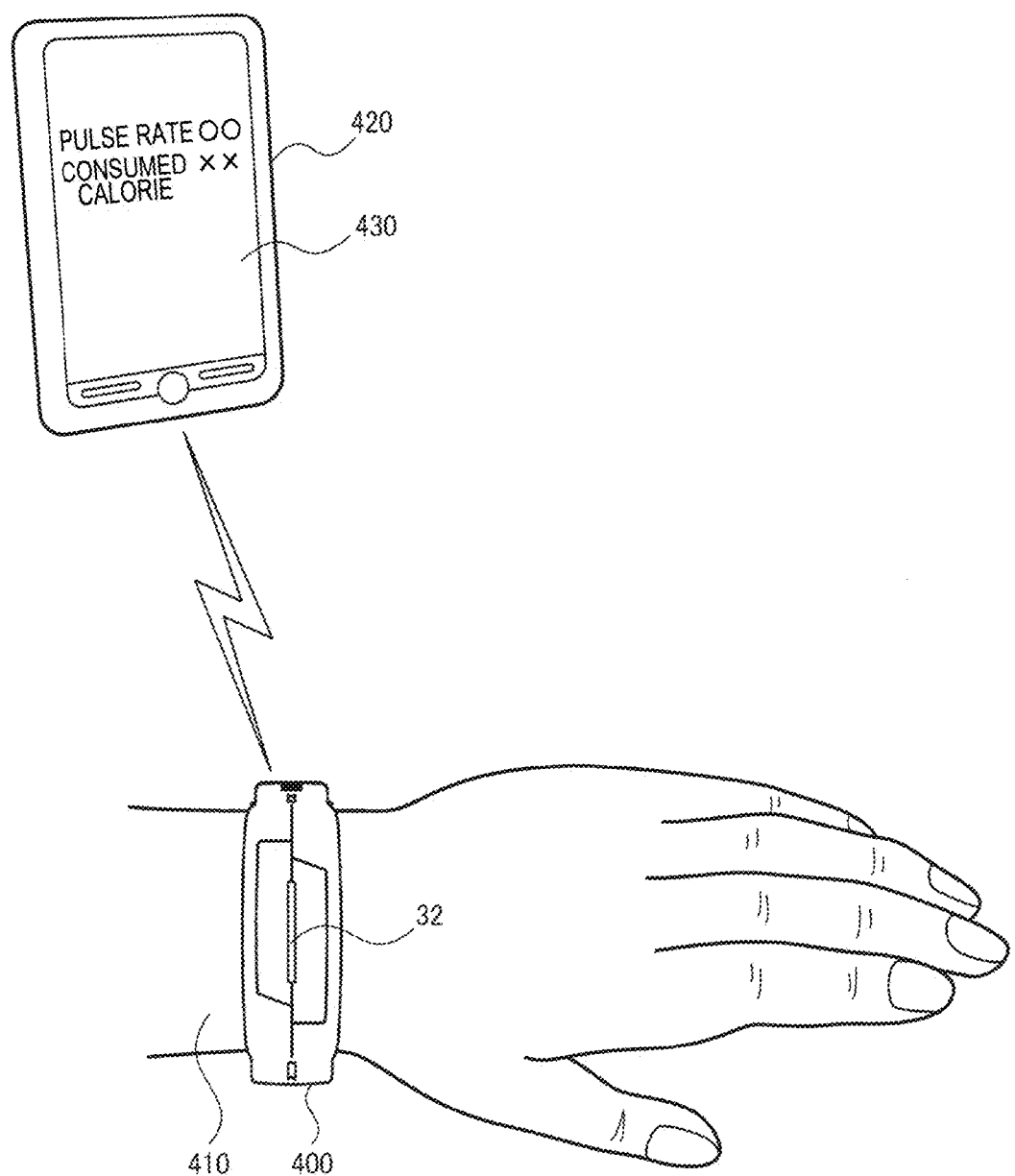
FIG. 4 is an explanatory diagram concerning wearing of the biological information detecting device and communication with a terminal apparatus.

FIG. 4 is an explanatory diagram concerning wearing of the biological information detecting device 400 and communication with a terminal device 420. As shown in FIG. 4, the user, who is a subject, wears the biological information detecting device 400 on a wrist 410 like a watch. As shown in FIG. 3, the pulse wave sensor section 40 is provided on the surface on the subject side of the case 30. Therefore, when the biological information detecting device 400 is worn, the pulse wave sensor section 40 comes into contact with and applies a pressing pressure to the skin surface of the wrist 410. In that state, the light emitting section 150 of the pulse wave sensor section 40 emits light and the light receiving section (at least one of the first light receiving section 141 and the second light receiving section 142) receives reflected light, whereby biological information such as a pulse wave is detected. Note that a wearing part may be an ankle, a finger, an upper arm, or the like.

The biological information detecting device 400 and the terminal device 420 are connected to communicate and are capable of exchanging data. The terminal device 420 is a portable communication terminal such as a smartphone, a cellular phone, or a feature phone. Alternatively, the terminal device 420 may be an information processing terminal such as a table computer. As the communication connection of the biological information detecting device 400 and the terminal device 420, near field wireless communication (NFC) such as Bluetooth (registered trademark) can be adopted. Since the biological information detecting device 400 and the terminal device 420 are connected to communicate in this way, various kinds of information such as a pulse rate and a consumed calorie can be displayed on a display section 430 (an LCD, etc.) of the terminal device 420. That is, various kinds of information calculated on the basis of a detection signal of the pulse wave sensor section 40 can be displayed. Computation processing for the information such as a pulse rate and a consumed calorie may be executed in the biological information detecting device 400. Alternatively, at least a part of the computation processing may be executed in the terminal device 420.

The light emission window section 32 is provided in the biological information detecting device 400. Various kinds of information are notified to the user by light emission (lighting or flashing) of the light emitting section for alarming. For example, when the user enters a fat burning zone or when the user exits the fat burning zone, this is notified by the light emission of the light emitting section via the light emission window section 32. When a mail or the like is received in the terminal device 420, the reception of the mail or the like is notified from the terminal device 420 to the biological information detecting device 400. The light emitting section of the biological information detecting device 400 emits light, whereby the reception of the mail or the like is notified to the user.

In the example shown in FIGS. 2A to 4, a display section such as an LCD is not provided in the biological information detecting device 400. Information that needs to be notified as characters, numbers, or the like is displayed on the display section 430 of the terminal device 420. In this way, in FIG. 4, the display section such as the LCD is not provided and necessary minimum information is notified to the user by the light emission of the light emitting section to realize a reduction in the size of the biological information detecting device 400. However, as explained below with reference to FIGS. 11A to 11F, a modified implementation in which the biological information detecting device 400 includes a display section such as an LCD or an organic EL display is also possible.

2.2 Functional Block Diagram

A functional block diagram of the biological information detecting device 400 in this embodiment is as shown in FIG. 1. In FIG. 1, the biological information detecting device 400 includes the pulse wave sensor section 40, a body motion sensor section (a body motion sensor device or a motion sensor device) 170, the processing section 200, a storing section (a memory) 240, a communication section 250, and an antenna 252. Note that the biological information detecting device 400 in this embodiment is not limited to the configuration shown in FIG. 1. Various modified implementations such as omission of a part of the components, replacement with other components, and addition of other components are possible.

The pulse wave sensor section 40 detects biological information such as a pulse wave. The pulse wave sensor section 40 includes the first light receiving section 141, the second light receiving section 142, and the light emitting section 150. However, the pulse wave sensor section 40 may include three or more light receiving sections. An example is shown in which the light emitting section 150 is shared by a plurality of light receiving sections. However, the light emitting section 150 is not limited to one light emitting section and may include two or more light emitting sections. The pulse wave sensor section 40 outputs, as detection signals (pulse wave detection signals), signals detected by a plurality of pulse wave sensors.

The body motion sensor section 170 outputs body motion information (body motion detection signals), which are signals changing according to body motion, on the basis of sensor information of various body motion sensors. The body motion sensor section 170 includes, for example, an acceleration sensor 172 as a body motion sensor. Note that the body motion sensor section 170 may include, as the body motion sensor, a pressure sensor, a gyro sensor, a position sensor such as a GPS receiver, or the like.

The processing section 200 performs various kinds of signal processing and control processing using, for example, the storing section 240 as a work region. The processing section 200 can be realized by a processor. The processor may be, for example, a CPU (Central Processing Unit). However, the processor is not limited to the CPU. Various processors such as a GPU (Graphics Processing Unit) and a DSP (Digital Signal Processor) can be used. The processor may be a hardware circuit formed by an ASIC (application specific integrated circuit). The processing section 200 includes an operation-mode-switching processing section 210 and a biological-information computing section 220.

The operation-mode-switching processing section 210 performs switching processing for the operation mode. Details are explained below.

The biological-information computing section 220 performs computation of biological information such as pulse wave information. For example, the biological-information computing section 220 performs noise reduction processing. In the double sensor mode, the biological-information computing section 220 performs first noise reduction processing for reducing (removing) noise from the first detection signal on the basis of the second detection signal. In a narrow sense, the first noise reduction processing is body motion noise reduction processing for reducing body motion noise. In the single sensor mode, the biological-information computing section 220 performs second noise reduction processing for reducing body motion noise from the first detection signal on the basis of body motion information acquired from the body motion sensor section 170. Note that, in the double sensor mode, the biological-information computing section 220 may perform both of the first noise reduction processing and the second noise reduction processing.

For example, the spectrum subtraction method only has to be used as the first noise reduction processing. The adaptive filter processing only has to be used as the second noise reduction processing. Details of the respective kinds of noise reduction processing are explained below.

The biological-information computing section 220 performs computation processing for biological information. The biological information is information such as a pulse rate. Specifically, the biological-information computing section 220 performs frequency analysis processing such as FFT on a detection signals after the noise reduction processing, calculates a spectrum, and performs processing for setting, as a frequency of a heart rate, a representative frequency in the calculated spectrum. A value obtained by multiplying the calculated frequency with 60 is a pulse rate (a heart rate) that is generally used. Note that the pulse wave information is not limited to the pulse rate itself and may be, for example, other various kinds of information representing the pulse rate (e.g., a frequency and a cycle of a heart beat and fluctuation in the frequency and the cycle). The pulse wave information may be information representing a state of a pulse. For example, a value representing a blood amount itself may be set as the pulse wave information.

The communication section 250 performs communication processing with the terminal device 420 on the outside as explained with reference to FIG. 4. The communication section 250 performs processing of wireless communication conforming to a standard such as Bluetooth (registered trademark). Specifically, the communication section 250 performs reception processing for a signal from the antenna 252 and transmission processing for a signal to the antenna 252. The function of the communication section 250 can be realized by a processor for communication or a logic circuit such as an ASIC.

2.3 Noise Reduction Processing

Figure 5A:
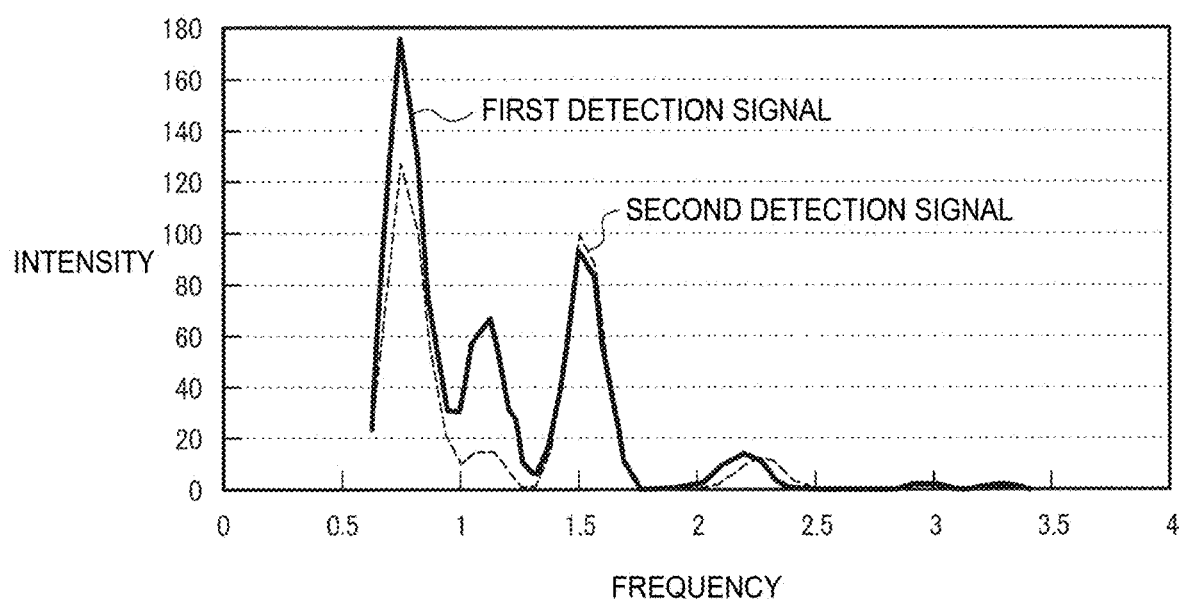
FIGS. 5A and 5B are diagrams for explaining body motion noise reduction processing using a second detection signal.
Figure 5B:
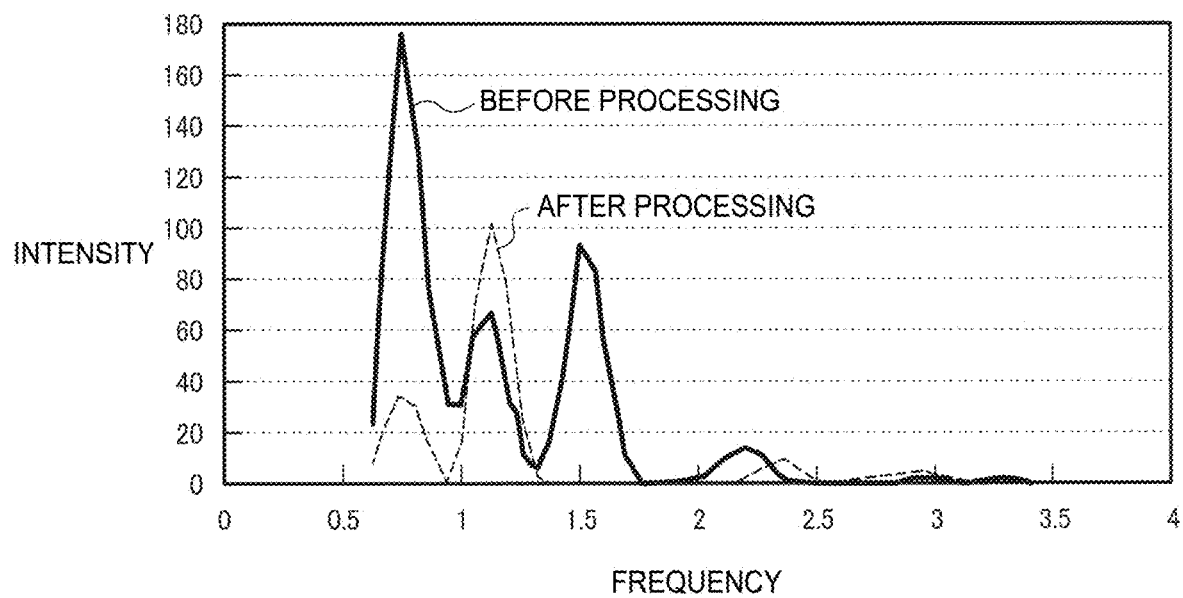

FIGS. 5A and 5B are diagrams for explaining noise reduction processing (first noise reduction processing) for the first detection signal based on the second detection signal using the spectrum subtraction method. In the spectrum subtraction method, frequency conversion processing is performed on the respective first and second detection signals to calculate spectra. Processing for estimating a noise spectrum from the spectrum of the second detection signal and subtracting the estimated noise spectrum from the spectrum of the first detection signal is performed.

In FIG. 5A, the spectrum of the first detection signal and the spectrum of the second signal, which are actually calculated, are shown. As explained above, the spectrum of the second detection signal is a spectrum corresponding to noise component when the biological information detecting device 400 according to this embodiment is used. That is, a frequency having a high peak in the spectrum of the second detection signal can be estimated as a frequency corresponding to body motion noise. Actually, in the spectrum of the second detection signal, only peaks may be subtracted. However, the noise reduction processing is not limited to this. For example, processing for subtracting the entire spectrum of the second detection signal from the entire spectrum of the first detection signal only has to be performed.

In the subtraction, for example, one of the first detection signal and the second detection signal is multiplied with a coefficient to offset noise. The coefficient is calculated from, for example, signal intensity of a predetermined frequency. Alternatively, it is also possible to separate the noise and the signals with a method such as clustering and calculate the coefficient to set the noise of the first detection signal and the noise of the second detection signal to the same intensity.

An example of the first detection signal before and after the noise reduction processing by the spectrum subtraction method is shown in FIG. 5B. As it is seen from FIG. 5B, body motion noise appearing at 0.7 to 0.8 Hz (42 to 48 in a pulse rate) and 1.5 Hz (90 in a pulse rate) is reduced by the body motion noise reduction processing. It is possible to reduce likelihood of erroneously determining that these kinds of body motion noise are pulse signals. On the other hand, concerning a spectrum corresponding to a pulse signal appearing before and after 1.1 Hz (66 in a pulse rate), it is possible to maintain a signal level without reducing the signal level.

The spectrum subtraction method is realized by frequency conversion processing such as FFT (Fast Fourier Transform) and subtraction processing in a spectrum. Therefore, there is an advantage that an algorithm is simple and computational complexity is small. Since there is no learning element unlike the adaptive filter processing explained below, there is a characteristic that instantaneous responsiveness is high.

Figure 6:
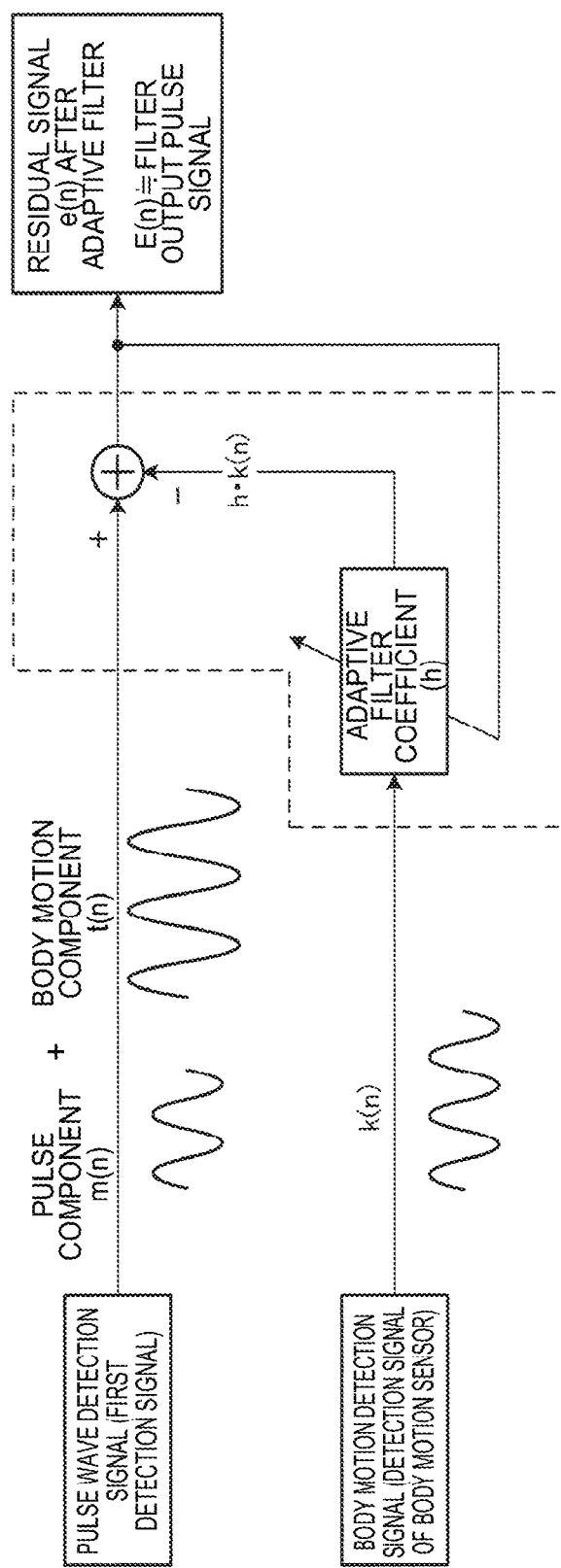
FIG. 6 is a diagram for explaining adaptive filter processing.

Body motion noise reduction processing (second noise reduction processing) based on a detection signal from a body motion sensor using the adaptive filter processing is explained. A specific example of the noise reduction processing using the adaptive filter processing is shown in FIG. 6. Specifically, the detections signal of the body motion sensor corresponds to body motion noise. Therefore, processing for subtracting, from the first detection signal, a noise component specified from the detection signal is performed. The idea of the noise reduction processing is roughly the same as the spectrum subtraction method.

However, even if both of the body motion noise in the pulse wave detection signal and the body motion detection signal acquired from the body motion sensor are signals due to the same body motion, signal levels of the body motion noise and the body motion detection signal are not always the same. Therefore, filter processing, in which a filter coefficient is adaptively determined for the body motion detection signal, is performed to calculate an estimated body motion noise component and calculate a difference between the pulse wave detection signal and the estimated body motion noise component. Since the filter coefficient is adaptively determined (by performing learning), it is possible to improve accuracy of the noise reduction processing. However, it is necessary to take into account a processing load in determination of the filter coefficient and a delay of an output. Note that, since the adaptive filter processing is a widely known method, detailed explanation is omitted.

In this embodiment, the biological information detecting device includes the body motion sensor section 170 (the acceleration sensor 172) as shown in FIG. 1. The processing section 200 performs, on the basis of a detection signal acquired from the body motion sensor section 170, second body motion noise reduction processing for reducing body motion noise of the first detection signal.

Note that the double sensor mode is based on the premise that the body motion noise reduction processing using the second detection signal is performed. However, the body motion noise reduction processing using the body motion sensor is not prevented from being concurrently used. Consequently, it is possible to more accurately reduce the body motion noise compared with when only the body motion noise reduction processing using the second detection signal is performed. For example, in FIG. 5B, noise at 0.7 to 0.8 Hz or 2.3 to 2.4 Hz is not fully reduced. However, it is also possible to reduce the noise by concurrently using the processing using the detection signal acquired from the body motion sensor section 170.

Figure 7:
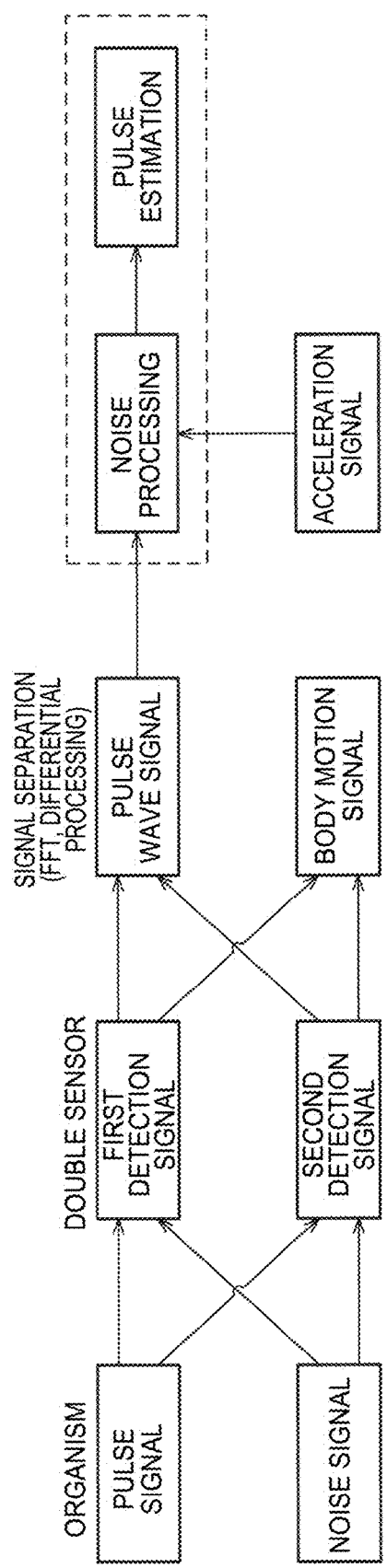
FIG. 7 is a diagram for explaining a flow of signal processing.

As shown in FIG. 7, it is possible to detect a pulse signal and a noise signal from an organism. Both of the pulse signal and the noise signal are included in each of a plurality of detection signals. However, in this embodiment, a ratio of the pulse signal and the noise signal is different for each of the detection signals. In the first detection signal, a ratio of the pulse signal is relatively high. In the second detection signal, a ratio of the pulse signal is low (a ratio of body motion noise is high) compared with the first detection signal. The pulse signal and a body motion signal (the body motion noise) are separated using the two detection signals. This processing is realized by the spectrum subtraction method. The second body motion noise reduction processing using body motion information (a body motion detection signal; in FIG. 7, an acceleration signal) of the body motion sensor is performed the separated pulse signal (the first detection signal after the body motion noise reduction processing). A pulse rate and the like are estimated from a result of the second body motion noise reduction processing.

3. Switching Of The Operation Mode

The switching processing for the operation mode performed by the processing section 200 (the operation-mode-switching processing section 210) is explained. First, switching processing based on a result of behavior determination processing using body motion information is explained. Thereafter, switching processing based on operation information is explained. Lastly, various modifications are explained.

3.1 Behavior Determination Processing

The processing section 200 of the biological information detecting device may perform the switching processing for the operation mode on the basis of a result of behavior determination processing for the user.

The result of the behavior determination processing is information indicating a behavior state of the user and is information indicating which of states such as a rest state and an exercise state the behavior state is. Alternatively, the states may be subdivided. As the exercise state, it may be discriminated what kind of exercise the user is specifically performing. In the following explanation, the behavior in this embodiment includes at least two of kinds of behavior shown in A1 in FIG. 9. The result of the behavior determination processing is information for specifying which of the kinds of behavior the behavior of the user is.

The behavior state of the user is strongly related to whether detection of biological information (pulse wave information) based on a detection signal acquired from the pulse wave sensor section 40 is easy. For example, in the rest state, since there is little body motion and body motion noise included in the detection signal is small, sufficient accuracy can be expected even if the biological information is calculated by relatively rough processing. On the other hand, in a state in which hard exercise is performed, since there is a lot of body motion, the body motion noise is large. Detection accuracy of the biological information is deteriorated unless the body motion noise is appropriately reduced. Further, whereas fluctuation in a pulse rate and the like is small in the rest state, in the exercise state, the pulse rate and the like could fluctuate in a certain degree of a large range. Therefore, in that regard as well, more highly accurate processing is requested in the exercise state.

That is, by performing the switching processing for the operation mode on the basis of the result of the behavior determination processing, it is possible to realize appropriate mode switching corresponding to a state of the body motion noise included in the detection signal.

Note that various methods are conceivable concerning how the behavior determination processing is performed. However, a body motion sensor for detecting body motion only has to be used. Specifically, the biological information detecting device includes the body motion sensor section 170. The processing section 200 performs the behavior determination processing on the basis of body motion information acquired from the body motion sensor section 170 and performs the switching processing for the operation mode on the basis of a result of the behavior determination processing.

The body motion sensor section 170 is a sensor for detecting movement of the user (a wearer of the biological information detecting device). For example, the acceleration sensor 172, a gyro sensor, and an atmospheric pressure sensor are conceivable. The body motion sensor section 170 in this embodiment may be configured from only one kind of sensor or may be realized by a combination of a plurality of kinds of sensors.

Consequently, the body motion sensor can be provided in a (wearable) biological information detecting device assumed to be worn by the user. Therefore, the body motion information can be set as information that reflects body motion of the user.

The processing section 200 of the biological information detecting device can be used for the behavior determination processing. Consequently, the acquisition of the body motion information and the behavior determination processing and the switching processing for the operation mode based on the behavior determination processing can be performed as closed processing in the biological information detecting device. However, the method in this embodiment is not limited to this. The processing section 200 may perform the switching processing for the operation mode on the basis of a result of the behavior determination processing acquired from an external apparatus.

The external apparatus is, for example, the terminal device 420 such as a smartphone as shown in FIG. 4. The external apparatus (the terminal device 420) is not limited to the smartphone and may be an apparatus such as a server system. Alternatively, a connection form is also possible in which the biological information detecting device is connected to the smartphone and the smartphone is connected to the server system. In that case, the behavior determination processing may be executed in the smartphone or may be executed in the server system.

In any case, it is possible to execute the behavior determination processing in an apparatus different from the biological information detecting device in this case. In the biological information detecting device assumed to be small and light, there is a strong limitation on processing performance of the processing section 200 and the battery. Therefore, it is possible to reduce the processing load by performing the behavior determination processing on the outside. Since it is assumed that a processing section of the server system or the like has relatively high performance, depending on a condition of a communication time, it is sometimes possible to acquire a behavior determination result at high speed.

Various kinds of information are conceivable as information acquired as the behavior determination processing result based on the body motion information. As an example, the information may be information indicating which of a state S1, which is a rest state, a state S2, which is an exercise state in which motion with low periodicity or continuity is performed, and a state S3, which is an exercise state in which motion with high periodicity and continuity is performed, the behavior state is. The periodicity indicates that similar motion appears at every predetermined interval. The continuity indicates that given motion (e.g., motion for one cycle in the periodicity) is continued for a certain degree of a long period.

First, from the viewpoint that, as body motion is larger, body motion noise is larger and more highly accurate processing is necessary, it is important to divide the rest state (S1) and the exercise states (S2 and S3). Switching processing for switching the operation mode to the single sensor mode in the rest state and switching the operation mode to the double sensor mode in the exercise states is the basic processing. However, there is also a scene in which the noise reduction processing is relatively easy even in the exercise state. The scene is the state S3 in which the motion with high periodicity and continuity is performed. When periodicity and continuity of exercise are high, it is assumed that periodicity and continuity of body motion noise caused by the exercise are also high. It is easy to reduce such periodic and continuous noise. Therefore, in the state S3, it is possible to use the single sensor mode even in the exercise state.

Figure 8:
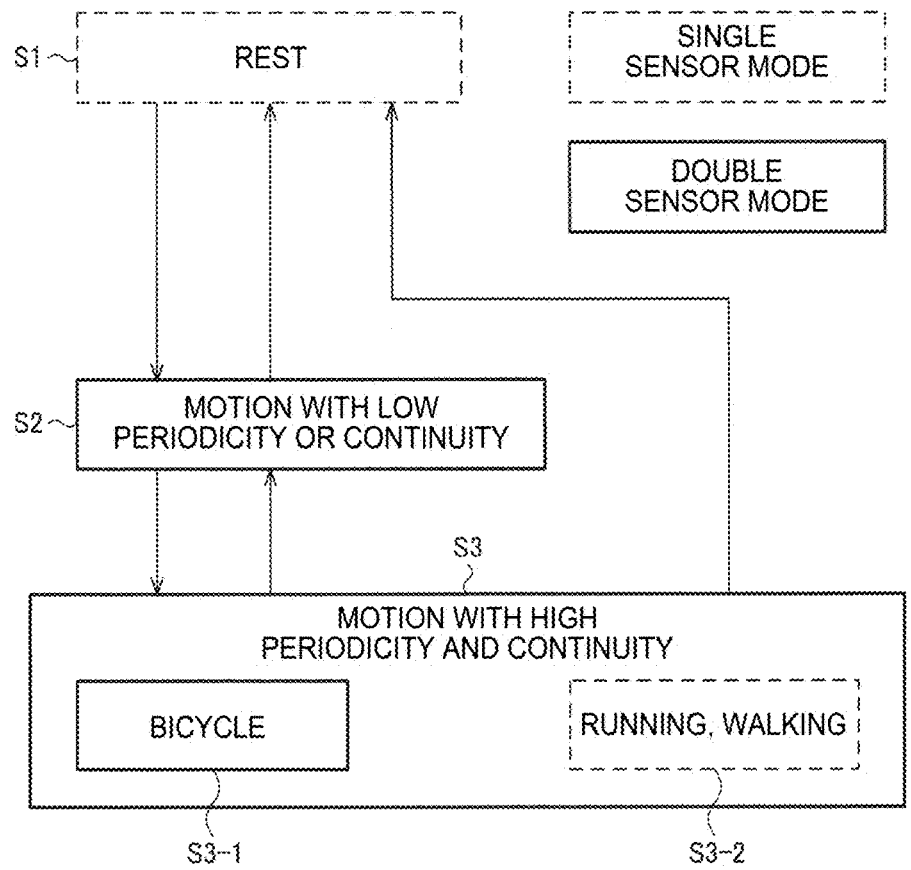
FIG. 8 is a state transition chart for explaining switching of an operation mode based on a result of behavior determination processing.

FIG. 8 is a state transition chart for explaining this processing. As explained above, S1 is the rest state, S2 is the exercise state and corresponds to the state in which the operation with low periodicity or continuity is performed, and S3 is the exercise state and corresponds to a state in which the operation with high periodicity and continuity is performed.

Transition from S1 to S2 is executed when the user starts to move the body from a state in which the user is not moving the body. Specifically, the transition corresponds to, for example, a start of movement from a stationary state in a daily activity. As an example, when an acceleration value (an absolute value or a square value of a given axis, a square sum of a plurality of axes, etc.) from an acceleration sensor exceeds a given threshold, the transition from S1 to S2 is performed. The operation mode only has to be switched from the single sensor mode to the double sensor mode according to the transition.

Note that, in FIG. 8, the transition to S2, that is, transition to a state in which the operation with low periodicity or continuity is performed is assumed be transition from the rest state S1. An example is shown in which direct transition to S3 is not performed. Therefore, even if the user starts exercise with high periodicity and continuity such as walking from the rest state, the behavior state transitions from the state S1 to the state S2 once. Thereafter, periodicity and continuity are determined. This is because, as explained above, the adaptive filter processing using the body motion information is assumed as the noise reduction processing executed in the single sensor mode.

In the adaptive filter processing, it is necessary to learn parameters of a filter. Therefore, after the start of the noise reduction processing, a certain degree of time (e.g., several seconds) is required until setting of appropriate parameters. As a result, immediately after body motion changes (e.g., immediately after the start of walking), the parameters are not values corresponding to the body motion. Highly accurate processing cannot be executed. When the behavior state directly transitions from S1 to S3, the single sensor mode is continued. Therefore, it is likely that detection accuracy of biological information is deteriorated immediately after the start of walking.

Therefore, in FIG. 8, it is determined whether the behavior state transitions from S1 to S2 and thereafter transitions to S3. Since it is assumed that the noise reduction processing (the adaptive filter processing) using the body motion information is performed even in the double sensor mode, in a period of S2, it is possible to perform learning of parameters for walking or running. It is possible to realize a smooth shift to the single sensor mode. Further, in the period of S2, the double sensor mode is used and the first noise reduction processing is performed. Therefore, it is possible to suppress accuracy deterioration in the period.

The transition from S2 to S3 is executed when the exercise with high periodicity and continuity is continued after the user starts to move the body. As an example, the frequency analysis processing such as FFT only has to be performed on acceleration information (a temporal change waveform) acquired from the acceleration sensor. In the case of exercise with high periodicity, a sharp peak appears at a specific frequency and a spread (fluctuation) of values decreases. Therefore, it is possible to determine whether periodicity and continuity are high by comparing a parameter indicating sharpness or the like of a graph and a given threshold.

In other words, when a predetermined frequency component corresponding to repetitive exercise is detected, the processing section 200 only has to switch the operation mode from the first operation mode (the double sensor mode) to the second operation mode (the single sensor mode). The repetitive exercise is exercise in which exercise with high similarity is repeated in a unit of a predetermined period and corresponds to the walking and the running.

Alternatively, in the determination of periodicity and continuity, an autocorrelation of the acceleration information (the temporal change waveform) may be calculated. Exercise with high periodicity and continuity has a high correlation value. Therefore, it is possible to determine whether periodicity and continuity are high on the basis of comparison processing of the correlation value and a given threshold (e.g., 0.7). When the transition from S2 to S3 is performed, the operation mode only has to be switched from the double sensor mode to the single sensor mode according to the transition.

The transition from S3 to S2 is executed when periodicity and continuity of exercise change. For example, the transition is executed when the rhythm of exercise continued to that point greatly changes. The frequency analysis processing and the determination based on the autocorrelation may be performed. Alternatively, when moving speed of the user is acquired and it is detected that the speed greatly changes from a steady state in which a speed change is little, the behavior state may transition from S3 to S2. The moving speed can be acquired from a GPS (Global Positioning System) and the like besides an acceleration sensor and a gyro sensor. When the transition from S3 to S2 is performed, the operation mode is switched from the single sensor mode to the double sensor mode according to the transition.

The transition from S2 to S1 and the transition from S3 to S1 are executed when the movement of the body stops. As an example, the determination based on the magnitude of the acceleration value only has to be performed as explained above. When the transition from S2 to S1 is performed, the operation mode is switched from the double sensor mode to the single sensor mode. When the transition from S3 to S1 is performed, the single sensor mode is maintained.

However, the behavior determination processing and the switching processing for the operation mode based on the behavior determination processing are not limited to those explained above. For example, the state S3 may be subdivided and considered separately as an exercise state S3-1 by a bicycle and an exercise state S3-2 by running or walking.

Exercise itself by the bicycle has high periodicity and continuity. However, it is known that, since the exercise is movement performed by riding a vehicle, body motion noise caused by the exercise has a complicated characteristic compared with the running and the walking (e.g., a variety of frequency components are included). Therefore, even in the same exercise state having high periodicity and continuity, it is desirable to use the double sensor mode in the state S3-1 and use the single sensor mode in the state S3-2.

Therefore, when the determination of the transition from S2 to S3 is performed, it is desirable to not only simply determine periodicity and continuity but also determine whether the exercise is exercise by a bicycle or walking or running (from another viewpoint, whether the exercise state is an exercise state by a vehicle). As a specific determination method, various methods such as Patent Literature 2 are known. In this embodiment, the methods can be widely applied. Therefore, detailed explanation of the methods is omitted.

When it is determined that the exercise state is the exercise state by the bicycle, the behavior state only has to transition from S2 to S3-1. The double sensor mode only has to be maintained as the operation mode. When it is determined that the exercise state is the exercise state by walking or running, the behavior state only has to transition from S2 to S3-2. The operation mode only has to be switched from the double sensor mode to the single sensor mode.

Figure 9:
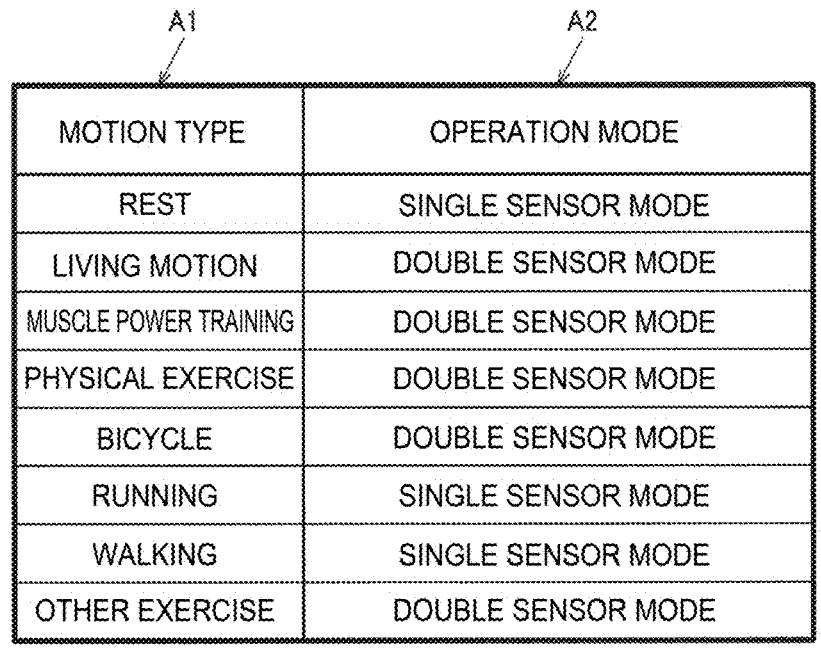
FIG. 9 is a relation example between the result of the behavior determination processing and the operation mode.

Alternatively, Patent Literature 2 discloses a method of more finely determining behavior of the user as shown in A1 in FIG. 9. In this embodiment, the operation mode may be switched on the basis of a result determined by the method. A2 of FIG. 9 is an example of a specific operation mode. The operation mode is switched to the single sensor mode in the rest state and the exercise state by running or walking and is switched to the double sensor mode in the other states.

Note that a state in which living motion is performed is a state in which deskwork, housekeeping, or the like is performed. The state is not a rest but movement is little compared with exercise states such as training and running. Therefore, from the viewpoint that movement is smaller than the movement in the exercise state, the living motion state can be set as the single sensor mode. From the viewpoint that movement is larger than the movement in the rest state, the living motion state can be set as the double sensor mode. In other words, various modified implementations are possible concerning where a threshold is set in switching of the single sensor mode and the double sensor mode according to the magnitude of body motion.

Figure 10:
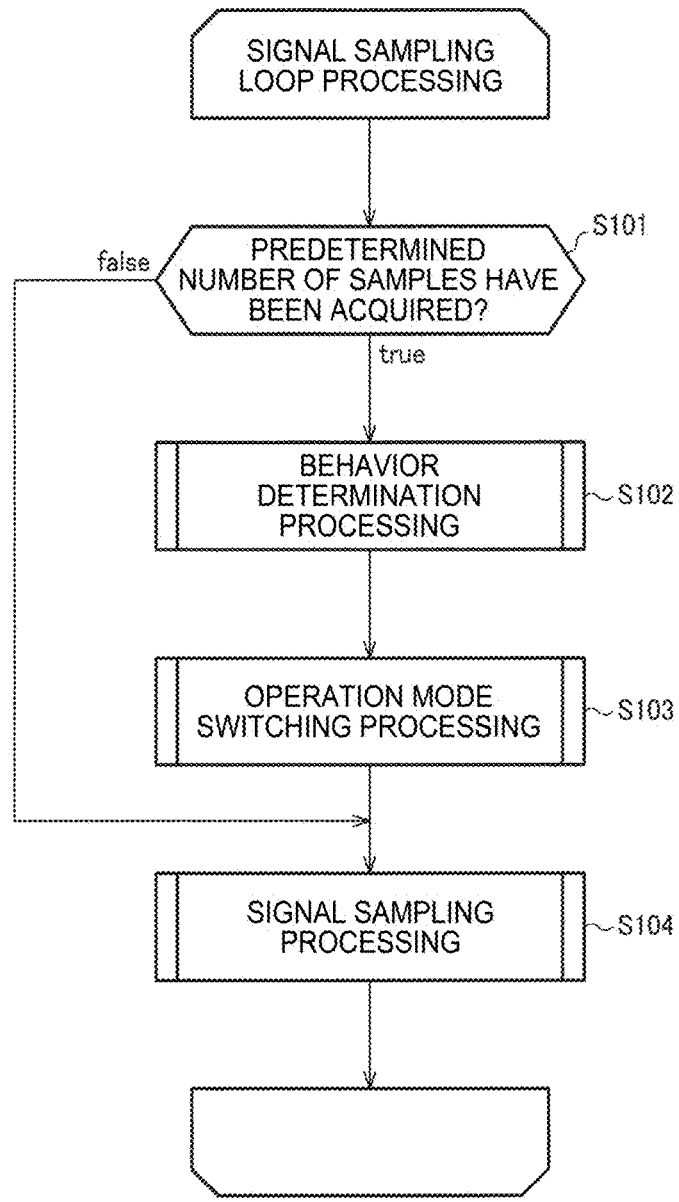
FIG. 10 is a flowchart for explaining switching of the operation mode based on the result of the behavior determination processing.
Figure 11A:
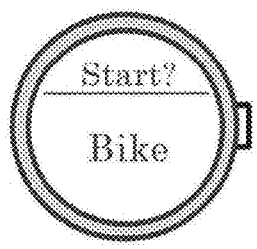
FIGS. 11A to 11F are display screen examples in an exercise measurement mode.
Figure 11B:
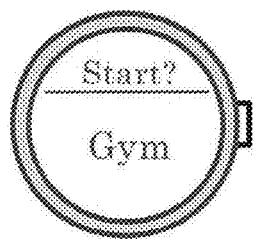
Figure 11C:
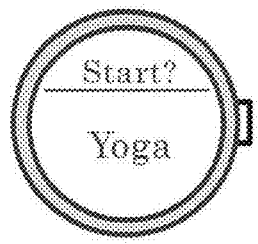
Figure 11D:
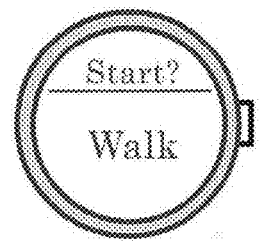
Figure 11E:
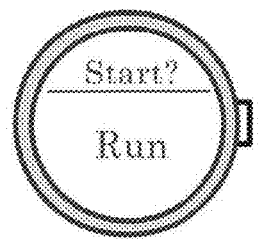
Figure 11F:

In FIG. 10, a flowchart for explaining operation mode switching processing in this embodiment is shown. When the processing is started, first, it is determined whether data of a predetermined number of samples has been acquired (S101). The data is data acquired in processing in S104 explained below, for example, body motion information such as a pulse signal (one or both of the first detection signal and the second detection signal) and an acceleration signal.

In the case of Yes in S101, the behavior determination processing is performed (S102). That is, FIG. 10 is an example in which the behavior determination processing is executed every time data is acquired by the predetermined number of samples. The processing in S102 only has to be performed on the basis of the body motion information such as an acceleration signal and a GPS signal as explained above.

The switching processing for the operation mode is performed on the basis of a processing result in S102 (S103). S103 can be realized by processing for performing, for example, transition conforming to the state transition chart shown in FIG. 8 and switching the operation mode according to a transition destination.

After the processing in S103, signal sampling processing is performed (S104). In the case of No in S101, that is, at timing different from acquisition timing for the predetermined number of samples, the behavior determination processing and the switching processing for the operation mode are not executed. After the processing in S104, the processing returns to S101 and loop processing is executed.

Note that, in FIG. 10, the switching processing for the operation mode is executed in a unit of the predetermined number of samples. However, it is also possible to execute the switching processing for the operation mode in every predetermined time irrespective of a sampling rate. When acquisition rates of signals are different, the "predetermined number of samples" may be set as the number of samples of a pulse signal or may be set as the number of samples of an acceleration signal. Various modified implementations are possible.

As explained above, the processing section 200 according to this embodiment performs, when it is determined on the basis of the result of the behavior determination processing for the user that the user has changed to the running state or the walking state, the switching processing for switching the operation mode from the first operation mode (the double sensor mode) to the second operation mode (the single sensor mode). Note that, in movement by the feet of the user, a state in which there is an instance when both the feet simultaneously leave the ground is the running state and a state in which one of the feet always touches the ground is the walking state.

Consequently, when it is determined that the user is performing running or walking, it is possible to switch the operation mode to the single sensor mode and reduce power consumption. The running or the walking is a special situation in which, although the running or the walking is an exercise state, the noise reduction processing is easy because periodicity and continuity are high. However, the method in this embodiment is appropriately adaptable to such a special situation.

The processing section 200 may set the operation mode to the second operation mode until a given time elapses after it is determined that the user has changed to the running state or the walking state on the basis of the result of the behavior determination processing for the user and switch the operation mode to the first operation mode after the given time elapses.

In the example shown in FIG. 8, the processing can be realized by a processing procedure for transitioning from S1 to S2 once and thereafter transitioning to S3 (in particular, S3-2 corresponding to walking or running). Consequently, in the adaptive filter processing executed in the first operation mode (the single sensor mode), time for performing appropriate learning can be secured. Therefore, it is possible to suppress accuracy deterioration of the noise reduction processing and the biological information detection processing.

3.2 Operation Information

The processing section 200 according to this embodiment may perform the switching processing for the operation mode on the basis of operation information of the biological information detecting device. The operation information is information acquired on the basis of operation of an operation section by the user. In a narrow sense, the operation section is an operation section provided in the biological information detecting device. Various forms such as a button, a lever, and a touch panel are conceivable. The operation section may be provided in a device different from the biological information detecting device or may be an operation section of, for example, the terminal device 420 shown in FIG. 4. In this case, operation information for instructing operation on the biological information detecting device is generated using the operation section of the terminal device 420. The biological information detecting device acquires the operation information via a network. The network may be realized by, for example, the near field wireless communication or may be realized by anther network such as the Internet.

When the operation information is used, for example, the biological information detecting device may include a plurality of measurement modes. Setting of the measurement modes may be performed according to the operation information. For example, the processing section 200 is capable of setting a plurality of measurement modes including at least two of an exercise measurement mode, a daily mode, and a sleep mode as the measurement modes of the biological information detecting device. The processing section 200 performs the switching processing for the operation mode on the basis of the set measurement modes.

The measurement modes are modes for setting in what kind of situation biological information (pulse wave information) is measured. Operation contents and the like of the sections (in particular, the sections related to detection processing for biological information) of the biological information detecting device are determined on the basis of the set measurement modes. The exercise measurement mode is a mode set when the user performs some kind of exercise. As an example, the exercise measurement mode is set by, when the user starts exercise, performing operation indicating to that effect. The sleep mode is a mode set during sleep. The sleep mode is set by performing, for example, at bedtime, operation indicating to that effect. The daily mode is a mode that is neither the measurement mode nor the sleep mode and is a mode set when the user performs daily life activities such as work and housekeeping or takes a rest. Operation for setting the measurement mode to the daily mode may be performed. The measurement mode may be set to the daily mode when operation for releasing the exercise measurement mode and the sleep mode is performed. Switching between the daily mode and the sleep mode may be automatic switching based on a body motion sensor or behavior determination processing.

As explained above, in the exercise state in which it is assumed that body motion is large, it is desirable to set the operation mode to the double sensor mode. Therefore, when it is determined on the basis of the operation information that the measurement mode is the exercise measurement mode, the processing section 200 switches the operation mode to the first operation mode.

In the sleep mode, since noise is little and biological information such as a pulse rate is stable, the operation mode only has to be set to the second operation mode (the single sensor mode). Concerning the daily mode, as explained above, both of the double sensor mode and the single sensor mode can be set. For example, it is also possible to acquire (for example, the user inputs), beforehand, information concerning whether the user mainly performs deskwork or mainly performs standing work and determine the operation mode corresponding to the daily mode on the basis of the information.

Note that, as explained in the example of the bicycle, the walking, or the running, in the exercise state, there are motion for which the double sensor mode is suitable and motion for which the single sensor mode is sufficient. Therefore, when transitioning to the exercise measurement mode (a workout mode), the biological information detecting device may cause the user to perform selection of a more specific exercise type. In other words, the biological information detecting device may request the user to input operation information for designating an exercise type.

As an example, the transition to the exercise measurement mode, display of a selection screen shown in FIGS. 11A to 11F is performed. Note that FIGS. 11A to 11F are plan views of observation of the main body section (the case section 30; a dial portion of a watch) of the biological information detecting device. Unlike the example shown in FIGS. 2A to 3, a biological information detecting device including a display section and an operation section (an operation button) is assumed. A bicycle can be set in FIG. 11A, a gym (e.g., equivalent to muscle training or the like in a training gym) can be set in FIG. 11B, yoga can be set in FIG. 11C, walking can be set in FIG. 11D, running can be set in FIG. 11E, and any other exercise can be set in FIG. 11F. Screens shown in FIGS. 11A to 11F can be selected (transition) according to, for example, operation of the operation section. By performing start operation in a state in which a desired exercise type is displayed, an exercise type corresponding to the desired exercise type is decided.

When the exercise type is decided, the operation mode is switched on the basis of the exercise type. As explained above, in walking or running (FIG. 11D or FIG. 11E), the operation mode only has to be switched to the single sensor mode. In the other exercise types, the operation mode only has to be switched to the double sensor mode. In a broad sense, in exercise for using fingers hard, the operation mode only has to be set to the double sensor mode. In exercise for only waving a hand, the operation mode only has to be set to the single sensor mode.

Note that the processing based on the operation information may be executed immediately (in an event driven manner) when the operation information is acquired. Alternatively, as in the flowchart shown in FIG. 10, it is also possible to determine an acquisition situation of the operation information at timing such as every acquisition of a predetermined number of samples or at every predetermined time and perform the switching processing for the operation mode when it is determined that the operation information is acquired at the timing.

3.3 Modifications

The method of performing the behavior determination processing and the method based on the operation information are explained above. Both of the methods may be used in combination instead of limiting the use of the methods to the use of only one of the methods. Various combinations are conceivable as a specific combination method. An example is explained below.

The operation information is information having relatively high reliability because the operation information is based on operation of the user. Therefore, when the double sensor mode is set as a necessary measurement mode (e.g., the exercise measurement mode in which the exercise type is other than walking or running) according to the operation information, the operation mode is set to the double sensor mode irrespective of a behavior determination result (e.g., without performing the behavior determination processing itself). When the doubles sensor mode is set as the other measurement modes, the switching processing for the operation mode based on the behavior determination result is performed.

Consequently, in a scene in which it is assumed that body motion noise is large, it is possible to secure accuracy by actively shifting to the double sensor mode. In other scenes, since sufficient possibility remains even in the single sensor mode, the operation mode is switched on the basis of the behavior determination result.

Alternatively, it is also possible to actively select the single sensor mode on the basis of the operation information. For example, when the measurement mode is set to the sleep mode, the operation mode may be set to the single sensor mode irrespective of the behavior determination result. Consequently, in a scene in which it is assumed that body motion noise is small, it is possible to reduce power consumption by actively shifting to the single sensor mode.

That is, as an example of the combination, it is possible to conceive a method of determining, on the basis of the operation information, (1) to set the operation mode to the double sensor mode irrespective of the behavior determination result, (2) to set the operation mode to the single sensor mode irrespective of the behavior determination result, or (3) to perform the mode switching processing based on the behavior determination result, and acquiring the behavior determination result when determining (3) performing the mode switching processing based on the behavior determination result.

In an exceptional situation explained below, switching processing for the operation mode not depending on both of the operation information and the behavior determination result may be executed.

For example, the biological information detecting device includes the communication section 250 that performs communication with the external apparatus. The processing section 200 performs the switching processing for the operation mode on the basis of communication situation information of the communication section 250. The communication situation information is information indicating a communication situation in the biological information detecting device (the communication section 250). The communication situation information may be, for example, information indicating whether the biological information detecting device is connected to the external apparatus or, when the external apparatus is connected, may be information capable of identifying a type and the like of the external apparatus. Alternatively, information indicating a continuous connection time with the external apparatus or information indicating a connection history in the past may be set as the communication situation information.

As the external apparatus, fitness equipment such as a treadmill and an ergometer set in a sports gym or the like and a cycle computer mounted on a road bike are conceivable. In this case, when the biological information detecting device is connected to the external apparatus, it can be determined that the user is performing (about to perform) hard exercise. Therefore, the operation mode is switched to the double sensor mode.

The processing section 200 may perform the switching processing of the operation mode on the basis of position information of the biological information detecting device.

For example, when it is determined on the basis of the position information that the user is present in a fitness gym or a park, it can be determined that the user is performing (about to perform) hard exercise. Therefore, the processing section 200 switches the operation mode to the double sensor mode. Alternatively, when it is determined that the user is present in a bedroom, the user is considered to be resting quietly (in a narrow sense, sleeping). Therefore, the processing section 200 switches the operation mode to the single sensor mode.

The processing section 200 may perform the switching processing for the operation mode on the basis of quality information of one detection signal of the first detection signal and the second detection signal.

Consequently, it is possible to perform the switching processing for the operation mode on the basis of a detection signal (a signal acquired from the pulse wave sensor section 40). For example, in a state in which the biological information detecting device is operating in the single sensor mode and acquiring the first detection signal, when it is determined that the quality of the first detection signal is deteriorated, the operation mode is switched to the double sensor mode irrespective of the operation information and the behavior determination result. This is because, in the first place, since the method in this embodiment is based on the premise that accuracy of biological information is secured, the deterioration in the quality of the first detection signal directly linked to the biological information is a serious problem.

Specifically, the processing section 200 may perform the switching processing for the operation mode on the basis of a determination result of autocorrelation information of one detection signal. That is, the processing section 200 may set a level of an autocorrelation as quality information of the detection signal. As the autocorrelation information, for example, a widely-known autocorrelation function (an autocorrelation coefficient) only has to be used. As a value of the autocorrelation function is larger (when the value is normalized, the normalized value is closer to a maximum value of 1), the correlation is higher and, as the value is smaller (when the value is normalized, the normalized value is closer to a minimum value of −1), the correlation is low.

The level of the quality corresponds to a level of noise with respect to the detection signal (further, a level of an SN ratio). The quality information is information indicating the level of the noise. In the case of walking and running, in view of the fact that noise having high periodicity is not a serious problem, a particular problem is noise having low periodicity and continuity. When such noise having low periodicity is mixed, a noise mixed part in a waveform of the detection signal has low correlation with other parts (noise non-mixed parts or other noise mixed parts). That is, the autocorrelation decreases. Therefore, it is possible to determine the quality of the detection signal using the autocorrelation. It may be determined whether the determination processing for the biological information (the pulse wave information) based on the detection signal is successful. If the quality is low, it is highly likely that the determination processing ends in failure. Therefore, it is possible to perform processing for regarding that the quality is low when the determination processing has ended in failure a predetermined number of times and switching the operation mode to the first operation mode.

The processing section 200 may perform the switching processing for the operation mode on the basis of battery residual capacity information of the battery included in the biological information detecting device.

As explained above, continuous use of the biological information detecting device according to this embodiment for a long period (ideally, all the time) is assumed as a life log. In that case, a significant disadvantage is that there is a period in which measurement itself is not performed. Therefore, when a battery residual capacity decreases (is equal to or smaller than a predetermined threshold), the operation mode is switched to the single sensor mode irrespective of the behavior determination processing, the operation information, and the like to extend battery life. The battery can be realized by various secondary batteries, super capacitors, and the like. The threshold for determining whether the battery residual capacity decreases changes according to a type of the battery. As an example, the operation mode only has to be switched to the second operation mode when a battery voltage decreases to 3.7 V or less.

The processing section 200 may set the operation mode to the second operation mode in a measurement preparation period and perform the switching processing for the operation mode in a period after the measurement preparation period.

The measurement preparation period is a preparation period before actual measurement of biological information is started. As an example, the measurement preparation period corresponds to a predetermined period after power-on of the biological information detecting device or a predetermined time after charging of the biological information detecting device is released (after the biological information detecting device is removed from a cradle).

If detection of biological information is performed only during exercise, since it is assumed that the biological information detecting device is correctly worn on the user during the power-on, the measurement preparation period may be not provided. However, when measurement of a life log is performed, if the measurement is suddenly started, in some case, the biological information detecting device is not worn. This is because, when the measurement is always performed, whereas a detection start of the biological information could be triggered by the power supply or the charging release rather than waiting for explicit operation by the user, the trigger does not guarantee appropriate wearing of the biological information detecting device by the user.

For example, when the biological information detecting device is not worn, in the first place, detection of appropriate biological information cannot be performed. Therefore, electric power is uselessly consumed even if the biological information detecting device is operated in the double sensor mode in such a case. Therefore, in this embodiment, it is also possible to provide the measurement preparation period and set the operation mode to the single sensor mode in the period. It is desirable to check a detection state of biological information, other signals, and the like in the measurement preparation period and, when it is determined that detection of biological information is possible, start the switching processing for the operation mode. However, a modified implementation for, for example, setting the measurement preparation period to a period having given fixed length is also possible.

The kinds of exceptional processing explained in this modification may or may not be respectively executed. Various methods are conceivable as a combination in executing a plurality of kinds of exceptional processing. For example, it is also possible to determine priority degrees of the kinds of exceptional processing in advance and, when contrary results are obtained in a given kind of exceptional processing and another kind of exceptional processing, specifically, when the single sensor mode is selected in one kind of exceptional processing and the double sensor mode is selected in the other kind of exceptional processing, adopt a result of the kind of exceptional processing having a higher priority degree. The switching processing may be immediately executed when conditions in the kinds of exceptional processing are satisfied (in an event driven manner with the determination result set as an event). It is also possible to execute the kinds of exceptional determination processing at timing such as every acquisition of a predetermined number of samples or every predetermined time and perform the switching processing for the operation mode when it is determined that a switching condition is satisfied at the timing.

4. Specific Example Of The Pulse Wave Sensor Section
4.1 Configuration Example

Figure 12A:
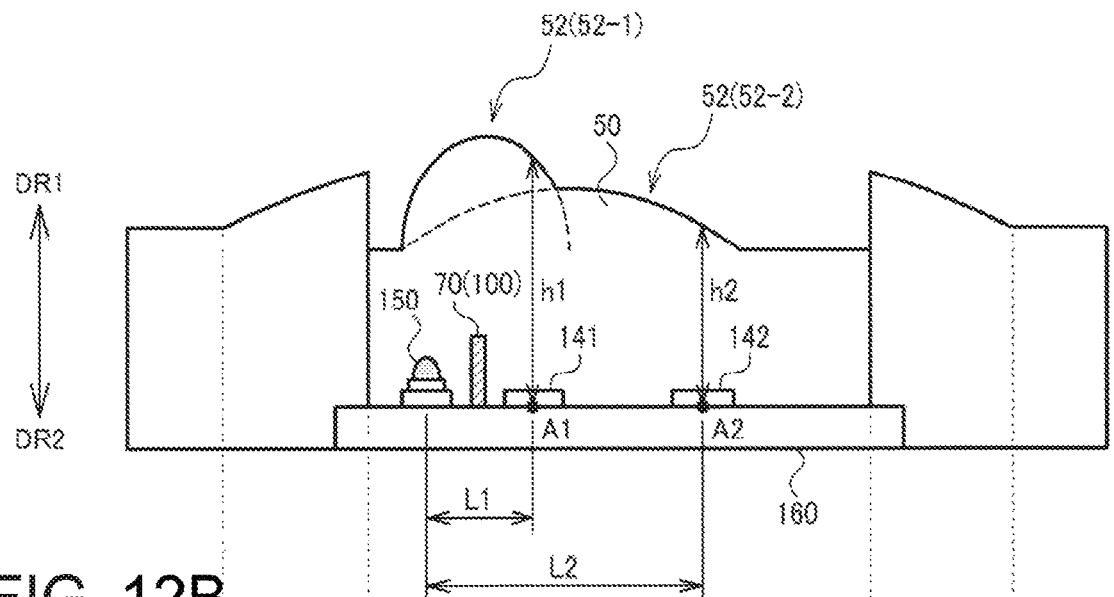
FIGS. 12A and 12B are a sectional view and a plan view showing a disposition example of first and second light receiving sections.
Figure 12B:
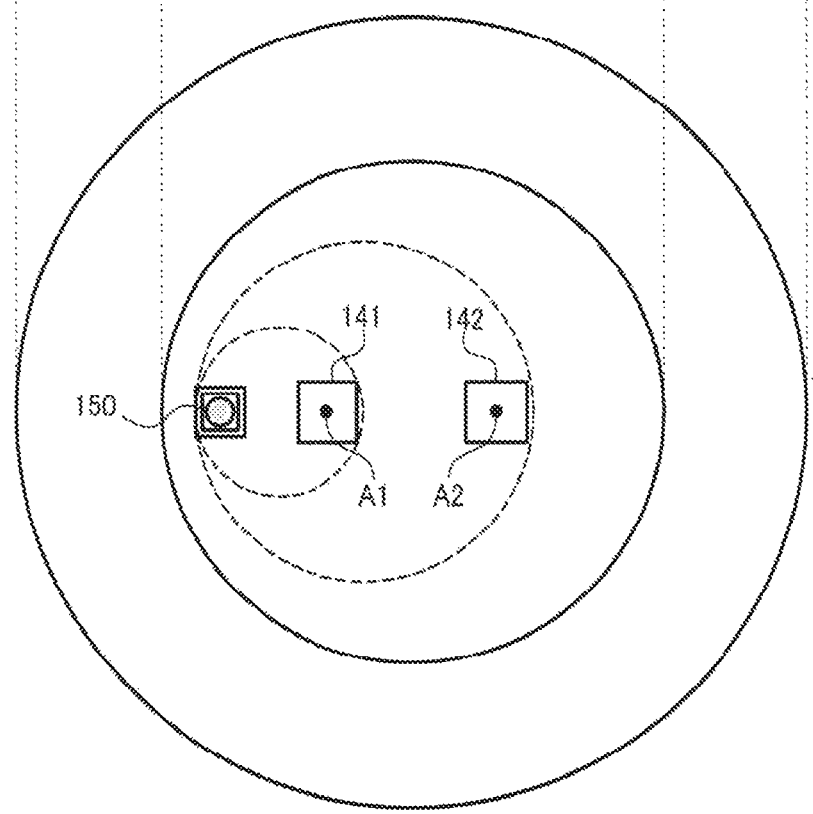
Figure 13:
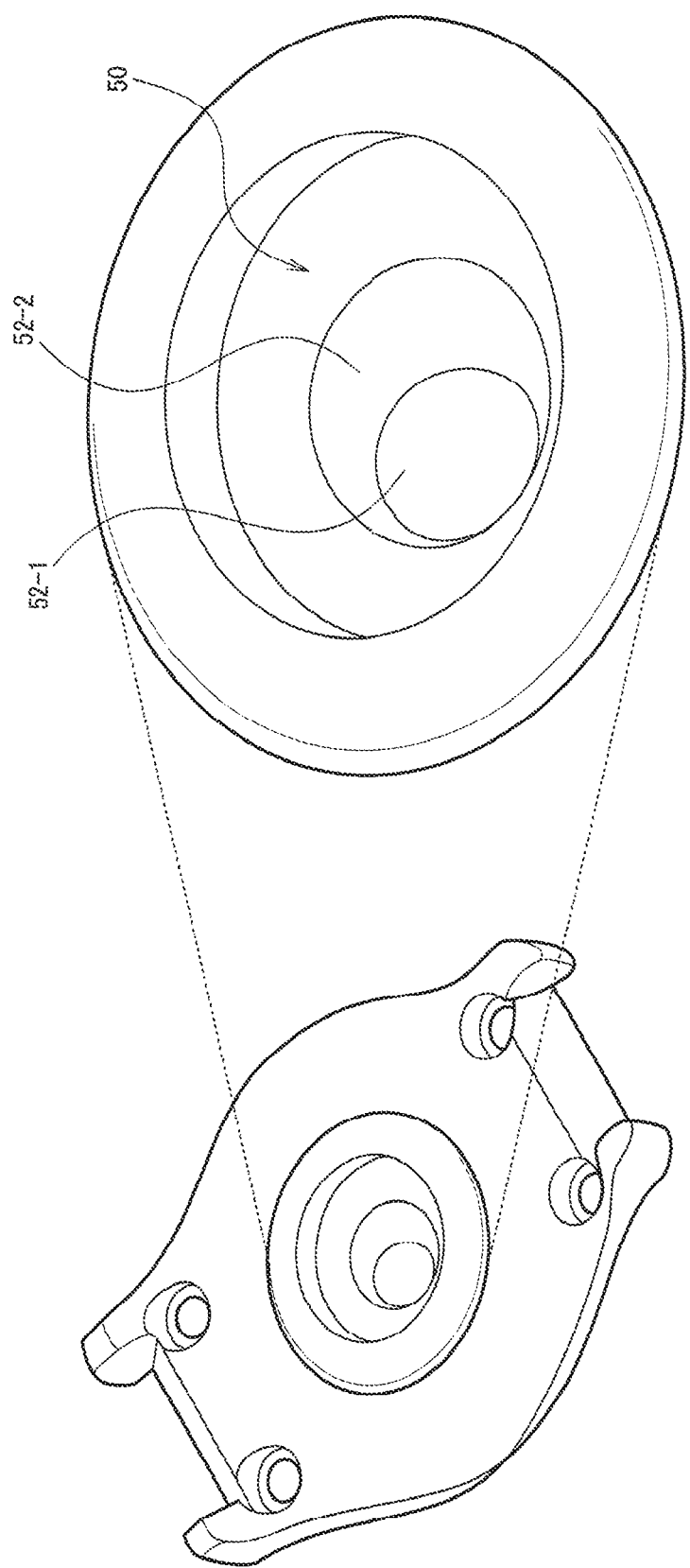
FIG. 13 is a perspective view showing the exterior of a pulse wave sensor section.

In FIGS. 12A, 12B, and 13, a detailed configuration example of the pulse wave sensor section 40 is shown. FIG. 13 is a perspective view of the pulse wave sensor section 40. FIG. 12A is a sectional view of the pulse wave sensor section 40. FIG. 12B is a plan view showing disposition of the light emitting section 150, the first light receiving section 141, and the second light receiving section 142 on aboard 160. FIG. 12B corresponds to a plan view in observation in a direction from the subject to the biological information detecting device (a direction of DR2) in a wearing state in FIG. 12A.

The pulse wave sensor section 40 includes the first light receiving section 141, the second light receiving section 142, and the light emitting section 150. The first light receiving section 141, the second light receiving section 142, and the light emitting section 150 are mounted on the board 160 (a sensor board). The first light receiving section 141 and the second light receiving section 142 receive light (reflected light, transmitted light, etc.) from the subject. The light emitting section 150 emits light to the subject. When the light emitting section 150 emits light to the subject and the light is reflected by the subject (the blood vessel), the first light receiving section 141 and the second light receiving section 142 receive and detect the reflected light.

The first light receiving section 141 and the second light receiving section 142 can be realized by light receiving devices such as photodiodes. The light emitting section 150 can be realized by a light emitting device such as an LED. For example, the first light receiving section 141 and the second light receiving section 142 can be realized by, for example, diode devices of PN junction formed on a semiconductor substrate. In this case, angle limiting filters for narrowing a light reception angle and wavelength limiting filters for limiting a wavelength of light made incident on the light receiving devices may be formed on the diode elements.

For example, in a pulsimeter, light from the light emitting section 150 travels on the inside of the subject and diffuses or scatters in a cuticle, a corium, a hypoderm, and the like. Thereafter, the light reaches the blood vessel (a region to be detected) and is reflected. At this point, apart of the light is absorbed by the blood vessel. An absorption rate of the light in the blood vessel changes and a light amount of the reflected light also changes because of the influence of the pulse. Therefore, the first light receiving section 141 receives the reflected light and detects the change in the light amount of the reflected light. Consequently, it is possible to detect a pulse rate and the like, which are biological information.

A member for light blocking 70 (a light blocking wall 100) is provided between the first and second light receiving sections 141 and 142 and the light emitting section 150. In the disposition shown in FIG. 12A, the light blocking wall 100 is provided between the first light receiving section 141 and the light emitting section 150. The member for light blocking 70 blocks, for example, the light emitted from the light emitting section 150 not to be directly made incident on the first light receiving section 141 and the second light receiving section 142.

The light transmitting member 50 is provided on a surface on a side of the biological information detecting device in contact with the subject and transmits light received from the subject. During measurement of biological information of the subject, the light transmitting member 50 is in contact with the subject. For example, the convex section 52 (a detection window) of the light transmitting member 50 is in contact with the subject. Note that the surface shape of the convex section 52 is desirably a curved surface shape (a spherical shape). However, the surface shape is not limited to this. Various shapes can be adopted. The light transmitting member 50 only has to be transparent with respect to a wavelength of the light received from the subject. A transparent material may be used or a colored material may be used as the light transmitting member 50.

Figure 14:
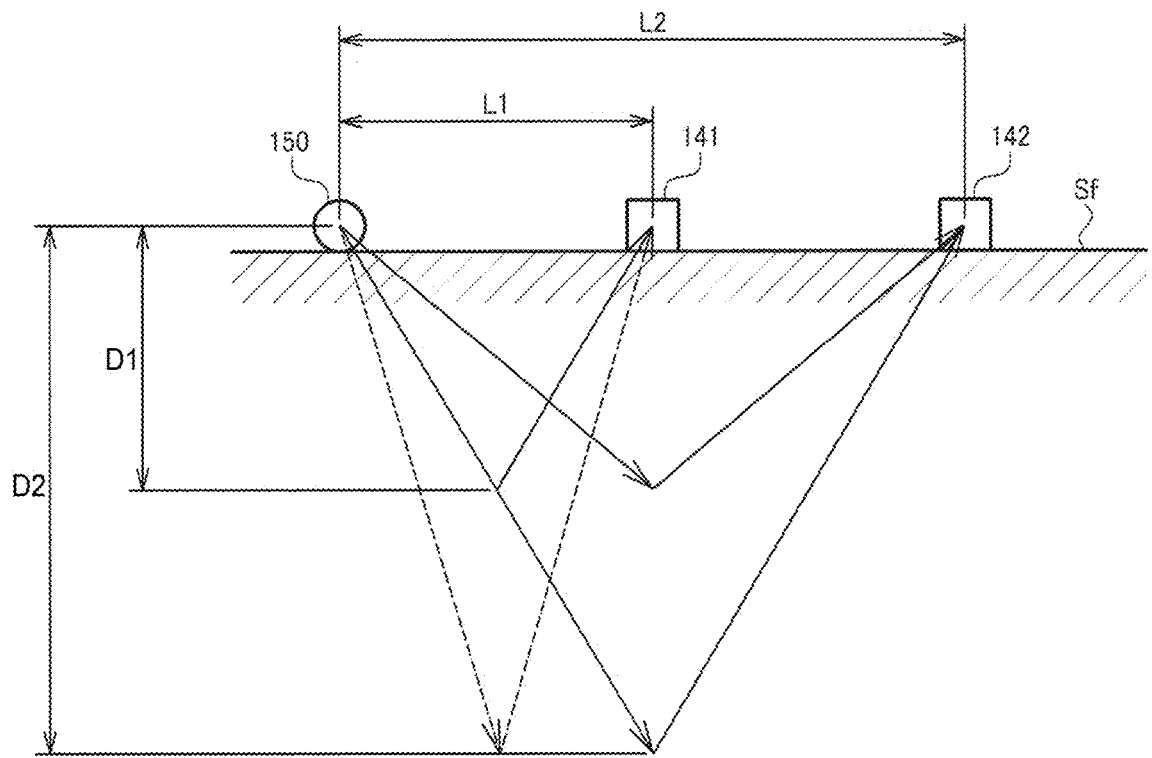
FIG. 14 is a diagram for explaining an influence of the distances between a light emitting section and light receiving sections on penetration depth of light.

4.2 Distances Between the Light Emitting Section and the Light Receiving Sections A distance L1 between the light emitting section 150 and the first light receiving section 141 and a distance L2 between the light emitting section 150 and the second light receiving section 142 are explained. FIG. 14 is a diagram for explaining an influence of the distances between the light emitting section and the light receiving sections on penetration depth of light. The light emitting section 150 and the first light receiving section 141 and the light emitting section 150 and the second light receiving section 142 are in contact with a skin surface Sf of the wrist of the user. As explained above, the light emitting section 150 is shared by two light receiving sections. Actually, as explained above, the light transmitting member 50 is in contact with the skin surface Sf. However, in FIG. 14, to simplify explanation, the light transmitting member 50 is omitted.

It is known that, as the distances between the light emitting section and the light receiving sections are shorter, sensitivity to a deep portion in an organism relatively decreases compared with sensitivity to a shallow portion. That is, the intensity of light radiated from the light emitting section 150, reflecting in the position of depth D1 in a biological tissue, and reaching the first light receiving section 141 is high compared with the intensity of the light reflecting in the position of depth D2 larger than the depth D1 and reaching the first light receiving section 141. On the other hand, the intensity of the light radiated from the light emitting section 150, reflecting in the position of the depth D1, and reaching the second light receiving section 142 is high compared with the intensity of the light reflecting in the position of the depth D2 and reaching the second light receiving section 142. However, the difference in the intensity in the second light receiving section 142 is not as large as the difference in the first light receiving section 141. Therefore, the first light receiving section 141 is suitable for measurement of a pulse wave in a blood vessel present in a position relatively shallower than the second light receiving section 142.

Figure 15:
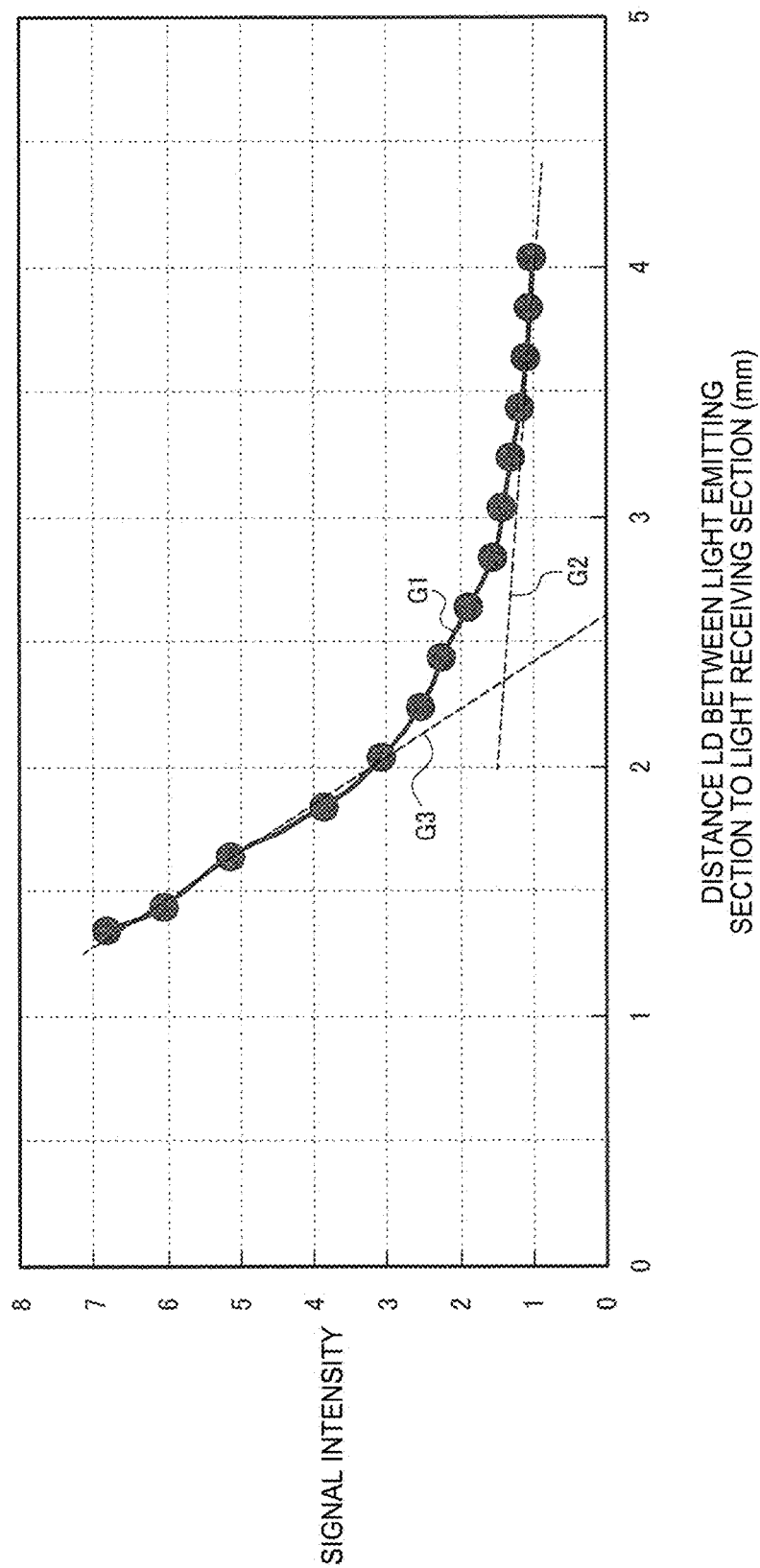
FIG. 15 is a diagram showing a relation between the distance between the light emitting section and the light receiving section and signal intensity of a detection signal.

FIG. 15 is a diagram showing a relation between a distance LD between the light emitting section 150 and the light receiving section and signal intensity. The distance LD between the light emitting section 150 and the light receiving section is, for example, the distance between the center positions (representative positions) of the light emitting section 150 and the light receiving section. For example, when the light receiving section has a rectangular shape (a substantially rectangular shape), the position of the light receiving section is the center position of the rectangular shape. When the light emitting section 150 includes a lens section and the like, the position of the light emitting section 150 is, for example, the center position of the lens section (the position of an LED chip).

As it is evident from FIG. 15, as the distance LD between the light emitting section 150 and the light receiving section is shorter, the signal intensity of a detection signal is higher and detection performance such as sensitivity is improved. Therefore, concerning the first light receiving section 141 that mainly detects a pulse signal, the distance LD between the first light receiving section 141 and the light emitting section 150 is desirably as close as possible.

Figure 16:
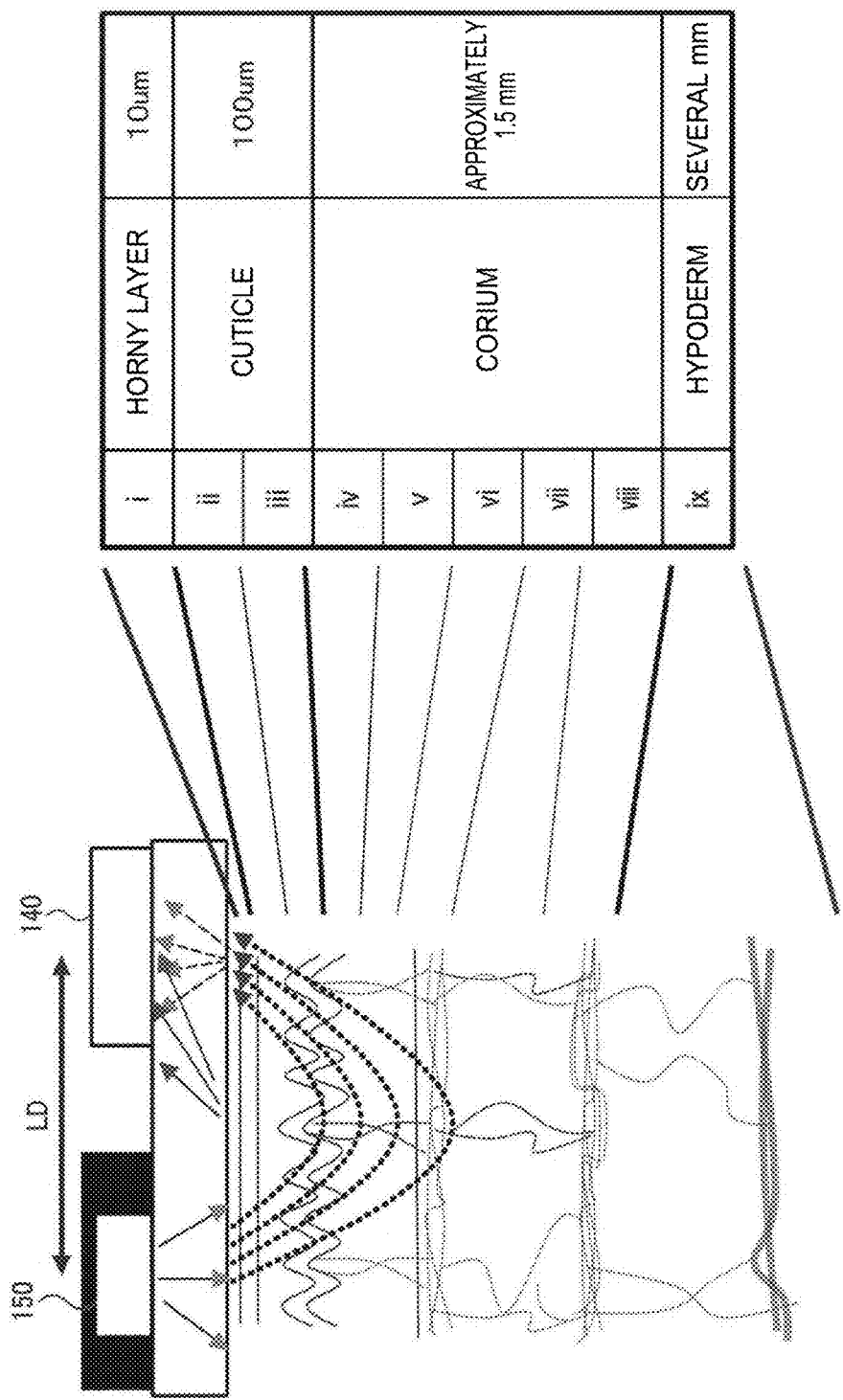
FIG. 16 is an explanatory diagram concerning a relation between the distance between the light emitting section and the light receiving section and a measured distance in a depth direction.

However, there is a lower limit value concerning the distance LD. It is undesirable to excessively reduce the distance LD. FIG. 16 is a schematic diagram showing a state in which light emitted from the light emitting section 150 reflects and scatters in an organism and a part of the light is received by the light receiving section. A relation of LD=2× LB generally holds between the distance LD between the light emitting section 150 and the light receiving section and a measured distance LB in the depth direction. That is, as the distance LD decreases, the measured distance LB in the depth direction also decreases according to the decrease in the distance LD. If a detection target object is absent in a range of the distance LB, a detection signal is extremely small.

Taking the above into account, in the pulse wave sensor section 40 in this embodiment shown in FIGS. 12A and 12B, for example, the distance L1 between the light emitting section 150 and the first light receiving section 141 is set to approximately 1.0 to 3.0 mm.

On the other hand, the distance L2 between the light emitting section 150 and the second light receiving section 142 only has to be set such that sensitivity to a pulse signal is low and sensitivity to body motion noise is high compared with the first light receiving section 141. For example, if L2<1.0 mm or 3.0 mm<L2, a degree of the pulse signal decreases and a degree of the body motion noise increases (an SN ratio decreases) compared with the first light receiving section 141 in which 1.0 mm≤L1≤3.0 mm.

Note that various modified implementations are possible concerning specific numerical values of L1 and L2, relationship between L1 and L2, and the like. However, the numerical values, the relationship, and the like are already publicly-known in Patent Literature 1 and the like. Therefore, more detailed explanation is omitted.

4.3 Pressing Pressure Difference

It is also known that sensitivity to a pulse signal and sensitivity to body motion noise change according to a pressing pressure on the subject as well.

Figure 17:
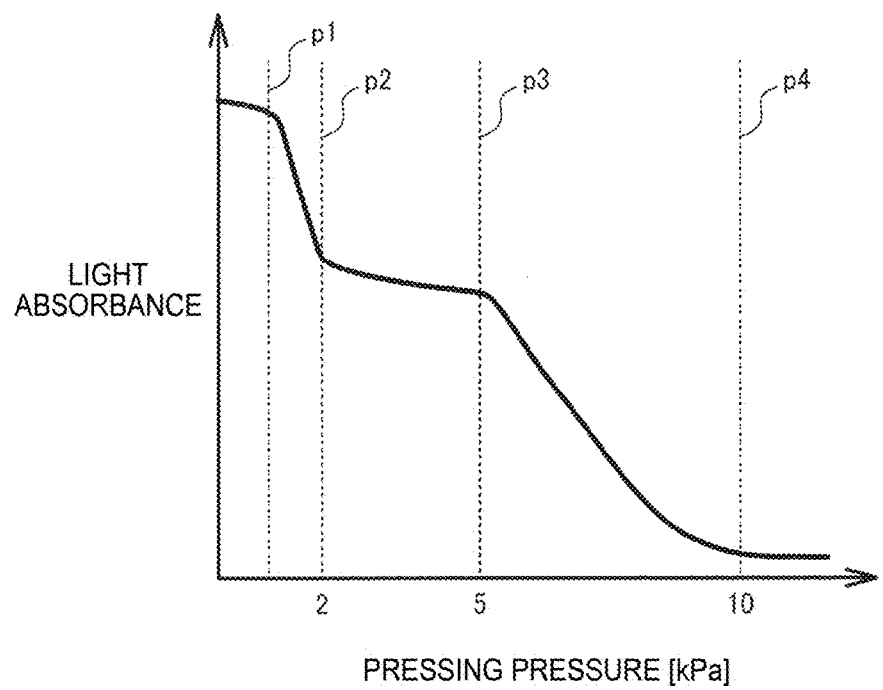
FIG. 17 is a diagram illustrating a change in light absorbance with respect to a pressing pressure.

FIG. 17 is a diagram illustrating a change in light absorbance with respect to a pressing pressure. The horizontal axis indicates the pressing pressure and the vertical axis indicates the light absorbance. When the pressing pressure changes, a blood vessel affected by the change in the pressing pressure changes. A blood vessel most easily affected, that is, affected by the lowest pressing pressure is a capillary. In an example shown in FIG. 17, a change amount of the light absorbance increases when the pressing pressure exceeds p1. This means that the capillary starts to be crushed by the pressing pressure. The change in the light absorbance becomes gentle when the pressing pressure exceeds p2. This means that the capillary is substantially completely crushed (closed). A blood vessel affected second most next to the capillary is an artery. When the pressing pressure further increases and exceeds p3, the change amount of the light absorbance increases again. This means that the artery starts to be crushed by the pressing pressure. The change in the light absorbance becomes gentle when the pressing pressure exceeds p4. This means that the artery is substantially completely crushed (closed).

In this embodiment, the second light receiving section 142 detects a signal corresponding to the capillary to increase a ratio of body motion noise. The first light receiving section 141 measures a signal (a pulse signal) corresponding to the artery to increase a ratio of the pulse signal. Therefore, the pressing pressure in the second light receiving section 142 is designed to fit within a range of p1 to p2. The pressing pressure in the first light receiving section 141 is designed to fit within a range of p3 to p4. A difference between the pressing pressures of the first light receiving section 141 and the second light receiving section 142 is desirably, for example, 2.0 kPa or more and 8.0 kPa or less.

Figure 18:
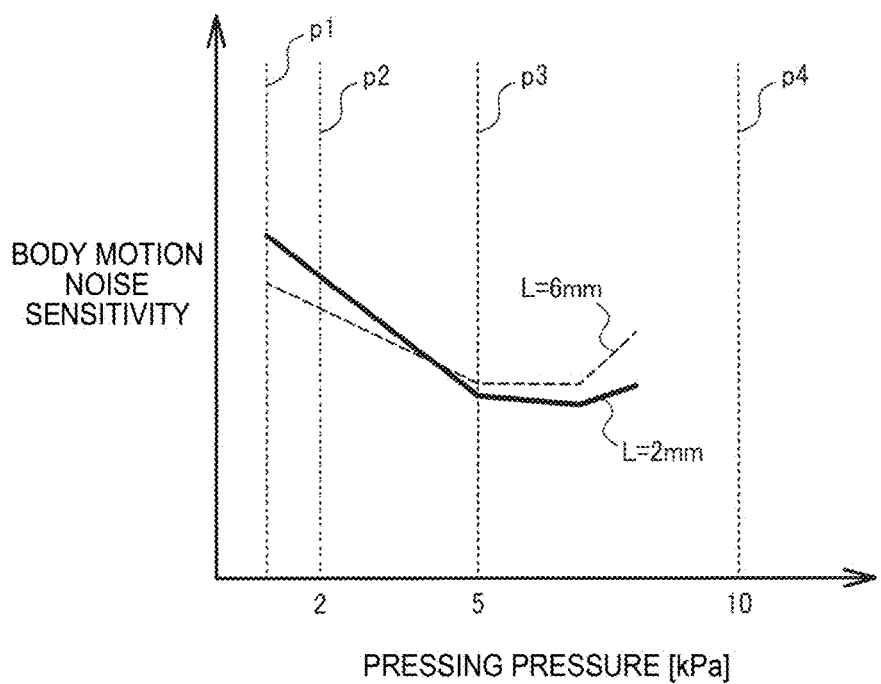
FIG. 18 is a diagram illustrating a change in body motion noise sensitivity with respect to the pressing pressure.

FIG. 18 is a diagram illustrating a change in the body motion noise sensitivity to the pressing pressure. In FIG. 18, both of an example in which a distance L from the light emitting section to the light receiving section is 2 mm and an example in which the distance L is 6 mm are shown. In both of the examples, as a tendency, the noise sensitivity is higher as the pressing pressure is lower and the noise sensitivity is lower as the pressing pressure is higher. This is considered to be because, since blood flowing in the capillary easily moves according to body motion, noise due to the body motion is easily carried on light reflected by the capillary present in a relatively shallow position in a biological tissue.

That is, during measurement of biological information of the subject, when a pressing pressure in a position or a region corresponding to the first light receiving section 141 in the light transmitting member 50 is represented as P1 and a pressing pressure in a position or a region corresponding to the second light receiving section 142 in the light transmitting member 50 is represented as P2, P1>P2. Consequently, it is possible to give a difference to characteristics between the first detection signal acquired from the first light receiving section 141 and the second detection signal acquired from the second light receiving section 142 as explained above.

Specifically, the difference between the pressing pressures only has to be realized by a difference in the height of the light transmitting member 50 that is in contact with the subject. As explained above, the pressing pressure is set high in the first light receiving section 141 that mainly detects a pulse signal. In the second light receiving section 142, the pressing pressure is set low compared with the first light receiving section 141. Therefore, height h1 of the light transmitting member in the position or the region corresponding to the first light receiving section 141 only has to be set high compared with height h2 of the light transmitting member in the position or the region corresponding to the second light receiving section 142.

Figure 19:
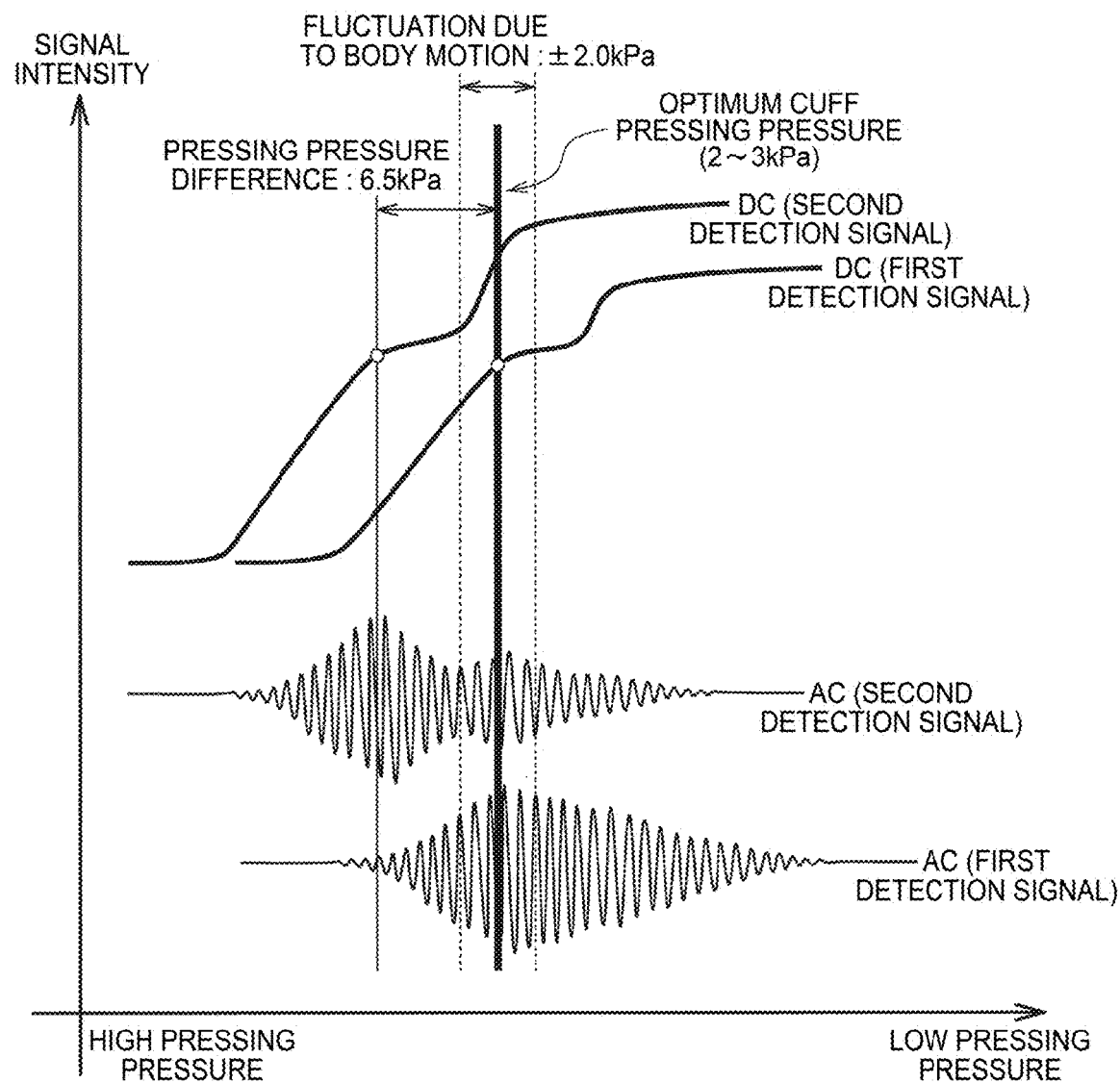
FIG. 19 is a relation diagram between a cuff pressing pressure and a DC component and an AC component detected by the light receiving sections.

This is because, as the first light receiving section 141 is higher, the first light receiving section 141 further projects to the subject side, and therefore, when the biological information detecting device is fixed to the wrist or the like at a given cuff pressure, a pressing pressure corresponding to the high first light receiving section 141 can be set high compared with a pressing pressure corresponding to the low second light receiving section 142. FIG. 19 shows this relationship.

The horizontal axis of FIG. 19 represents a cuff pressing pressure (in the biological information detecting device shown in FIG. 2A, pressure by the band section 10) and the vertical axis represents DC and AC components of a detection signal. As it is seen from DC signals shown in an upper part of FIG. 19, in the first light receiving section 141 in which the pressing pressure is relatively high, a certain degree of the pressing pressure is applied and the DC component is suppressed even in a state in which the cuff pressing pressure is relatively low. On the other hand, since the pressing pressure in the second light receiving section 142 is relatively low, a suppression degree of the DC component is small compared with the first detection signal in a state of the given cuff pressure. Therefore, in a range of an "optimum cuff pressing pressure" shown in FIG. 19, since the pressing pressure corresponding to the first light receiving section 141 fits within the range of p3 to p4, noise is suppressed and a signal level of the pulse signal increases. On the other hand, since the pressing pressure in the second light receiving section 142 fits within the range of p1 to p2, suppression of noise is insufficient and a ratio of the body motion noise increases.

This is also evident from comparison of AC components shown in a lower part of FIG. 19. In the range of the optimum cuff pressing pressure, a signal level of the AC component of the first detection signal is high and a signal level of the AC component of the second detection signal is low. As explained above, the pulse signal appears in a change of the detection signal, that is, the AC component. Therefore, FIG. 19 indicates that, whereas the first light receiving section 141 can sufficiently detect the pulse signal, the ratio of the body motion noise is relatively high in the second light receiving section 142.

A difference in the height of the light transmitting member 50 is explained in detail below with reference to the drawings. A perspective view, a sectional view, and a plan view of the pulse wave sensor section 40 are as shown in FIGS. 13, 12A, and 12B. As it is seen from FIGS. 12A to 13, the light transmitting member 50 includes the convex section 52 and applies, with the convex section 52, an appropriate pressing pressure to the subject.

In the biological information detecting device according to this embodiment, a plurality of photoelectric sensors (pulse wave sensors) are realized by providing a plurality of light receiving sections. Therefore, a plurality of (e.g., a number corresponding to the number of the photoelectric sensors) the convex sections 52 may be provided. In an example shown in FIG. 12A, a convex section 52-1 is provided for a first photoelectric sensor realized by the light emitting section 150 and the first light receiving section 141. A convex section 52-2 is provided for a second photoelectric sensor realized by the light emitting section 150 and the second light receiving section 142.

In this case, in a state in which the biological information detecting device is worn, when a direction from the biological information detecting device to the subject (DR1 in FIG. 12A) is set as the height direction, the height h1 of the light transmitting member in the position or the region corresponding to the first light receiving section 141 is high compared with the height h2 of the light transmitting member in the position or the region corresponding to the second light receiving section 142. This can also be realized by, for example, setting the height of the convex section 52-1 large compared with the height of the convex section 52-2. Note that various modified implementations are possible concerning how height is defined. For example, as shown in FIG. 12A, the distance from a surface on which the light emitting section 150 and the like are provided in the board 160 may be set as the height. Alternatively, the thickness itself of the light transmitting member 50 may be set as the height.

This embodiment is explained in detail above. However, those skilled in the art can easily understand that many modifications are possible without substantially departing from the new matters and the effects of the invention. Therefore, all such modifications are deemed to be included in the scope of the invention. For example, terms described together with broader-sense or synonymous different terms at least once in the specification or the drawings can be replaced with the different terms in any part of the specification or the drawings. The configurations and the operations of the biological information detecting device and the like are not limited to the configurations and the operations explained in this embodiment. Various modified implementations are possible.

What is claimed is:
1. A biological information detecting device comprising:
   at least one light emitting section configured to radiate light on a subject;
   a first light receiving section configured to receive light from the subject;
   a second light receiving section configured to receive the light from the subject; and a processing section configured to switch an operation mode between
- a first operation mode in which biological information is acquired on the basis of a first detection signal acquired from the first light receiving section and a second detection signal acquired from the second light receiving section, and
- a second operation mode in which the biological information is acquired on the basis of only one of the first detection signal and the second detection signal acquired by using only one of the first light receiving section and the second light receiving section.

2. The biological information detecting device according to claim 1, wherein the processing section switches the operation mode on the basis of a result of behavior determination processing for a user.

3. The biological information detecting device according to claim 2, wherein the processing section switches the operation mode from the first operation mode to the second operation mode when it is determined on the basis of the result of the behavior determination processing for the user that the user has changed to a running state or a walking state.

4. The biological information detecting device according to claim 3, wherein the processing section sets the operation mode to the first operation mode until a given time elapses after it is determined that the user has changed to the running state or the walking state on the basis of the result of the behavior determination processing for the user and switches the operation mode to the second operation mode after the given time elapses.

5. The biological information detecting device according to claim 2, further comprising a body motion sensor section, wherein
the processing section performs the behavior determination processing on the basis of body motion information acquired from the body motion sensor section and switches the operation mode on the basis of the result of the behavior determination processing.

6. The biological information detecting device according to claim 2, wherein the processing section switches the operation mode on the basis of a result of the behavior determination processing acquired from an external apparatus.

7. The biological information detecting device according to claim 5, wherein the processing section switches the operation mode from the first operation mode to the second operation mode when a predetermined frequency component corresponding to repetitive exercise is detected on the basis of the body motion information.

8. The biological information detecting device according to claim 2, wherein
the processing section is capable of setting, as a measurement mode of the biological information detecting device, a plurality of measurement modes including at least two of an exercise measurement mode, a daily mode, and a sleep mode, and
the processing section switches the operation mode on the basis of the set measurement mode.

9. The biological information detecting device according to claim 1, wherein the processing section switches the operation mode on the basis of operation information of the biological information detecting device.

10. The biological information detecting device according to claim 8, wherein the processing section switches the operation mode to the first operation mode when it is determined on the basis of the operation information that the measurement mode is the exercise measurement mode.

11. The biological information detecting device according to claim 1, further comprising a communication section configured to perform communication with an external apparatus, wherein
the processing section switches the operation mode on the basis of communication situation information of the communication section.

12. The biological information detecting device according to claim 1, wherein the processing section switches the operation mode on the basis of position information of the biological information detecting device.

13. The biological information detecting device according to claim 1, wherein the processing section switches the operation mode on the basis of quality information of one detection signal of the first detection signal and the second detection signal.

14. The biological information detecting device according to claim 13, wherein the processing section switches the operation mode on the basis of a determination result of autocorrelation information of the one detection signal.

15. The biological information detecting device according to claim 1, wherein the processing section switches the operation mode on the basis of battery residual capacity information of a battery included in the biological information detecting device.

16. The biological information detecting device according to claim 1, wherein the processing section sets the operation mode to the second operation mode in a measurement preparation period and switches the operation mode in a period after the measurement preparation period.

17. A control method for a biological information detecting device including: at least one light emitting section configured to radiate light on a subject; a first light receiving section configured to receive light from the subject; and a second light receiving section configured to receive the light from the subject,
the control method for the biological information detecting device comprising switching an operation mode between
- a first operation mode in which biological information is acquired on the basis of a first detection signal acquired from the first light receiving section and a second detection signal acquired from the second light receiving section, and
- a second operation mode in which the biological information is acquired on the basis of only one of the first detection signal and the second detection signal acquired by using only one of the first light receiving section and the second light receiving section.

18. The control method for the biological information detecting device according to claim 17, wherein the operation mode is switched on the basis of a result of behavior determination processing for a user.

19. The control method for the biological information detecting device according to claim 17, wherein the operation mode is switched on the basis of communication situation information of a communication section configured to perform communication with an external apparatus or battery residual capacity information of a battery.

20. The control method for the biological information detecting device according to claim 17, wherein the operation mode is switched from the first operation mode to the second operation mode when a predetermined frequency component corresponding to repetitive exercise is detected on the basis of body motion information acquired from a body motion sensor section.

* * * * *